(12) United States Patent
Ungpiyakul et al.

(10) Patent No.: US 6,909,106 B2
(45) Date of Patent: Jun. 21, 2005

(54) WEB VELOCITY-BASED REGISTRATION CONTROL SYSTEM

(75) Inventors: Tanakon Ungpiyakul, Neenah, WI (US); Thomas A. Bett, Oshkosh, WI (US)

(73) Assignee: Kimberly-Clark Worldwide, Inc., Neenah, WI (US)

(*) Notice: Subject to any disclaimer, the term of this patent is extended or adjusted under 35 U.S.C. 154(b) by 163 days.

(21) Appl. No.: 10/245,526

(22) Filed: Sep. 17, 2002

(65) Prior Publication Data

US 2004/0051059 A1 Mar. 18, 2004

(51) Int. Cl.$^7$ ............................................. G01N 21/86
(52) U.S. Cl. ............................... 250/559.4; 250/559.32
(58) Field of Search .................... 250/559.4, 559.44, 250/559.32, 221, 223 R; 356/27, 28, 634; 493/10, 11, 13

(56) References Cited

U.S. PATENT DOCUMENTS

| | | | |
|---|---|---|---|
| 4,264,957 A | * | 4/1981 | Pautzke ....................... 700/125 |
| 4,680,205 A | | 7/1987 | Lerner et al. |
| 4,837,715 A | | 6/1989 | Ungpiyakul et al. |
| 5,235,515 A | | 8/1993 | Ungpiyakul et al. |
| 5,359,525 A | | 10/1994 | Weyenberg |
| 5,659,538 A | | 8/1997 | Stuebe et al. |
| 5,802,974 A | | 9/1998 | McNeil |
| 6,245,168 B1 | | 6/2001 | Coenen et al. |

FOREIGN PATENT DOCUMENTS

| | | |
|---|---|---|
| GB | 987976 | 3/1965 |
| GB | 2 034 247 A | 6/1980 |
| GB | 2 088 340 A | 6/1982 |

* cited by examiner

*Primary Examiner*—Que T. Le
(74) *Attorney, Agent, or Firm*—Paul Yee; John L. Brodersen

(57) ABSTRACT

The present invention provides a method and apparatus (20) for controlling a registration between a target point (22) on a moving web (24), and a production outcome provided by a production operation. A method aspect can include a transporting of the web (24) along a movement direction (26) past a reference detector (30), and a detecting of at least a first reference point (50) on the web (24). The target point (22) can be designated by employing at least the first reference point (50). The web is transported past a speed-sensor (32), and the speed-sensor can measure a web speed of the moving web (24) to provide an output of web speed data. The web speed data is integrated over time to determine a web-length which has been transported past the speed-sensor (32). The production outcome is actuated at a production-device (34), and the actuating of the production outcome can be adjusted to occur after a reference-length of the web (24) has been transported past the speed-sensor (32).

20 Claims, 10 Drawing Sheets

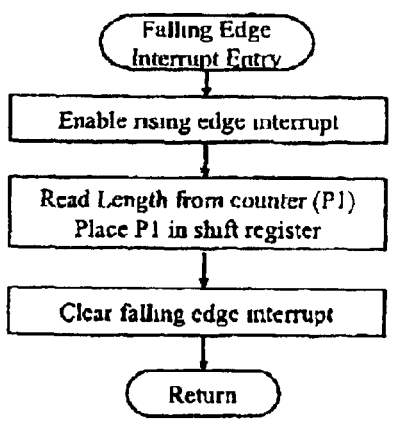
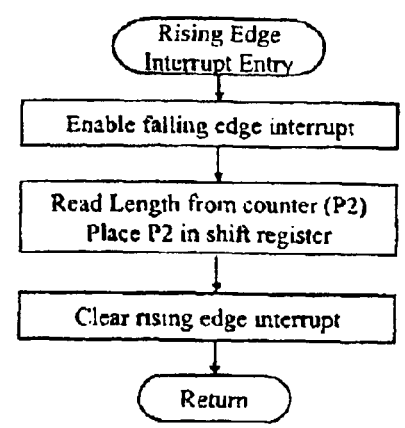
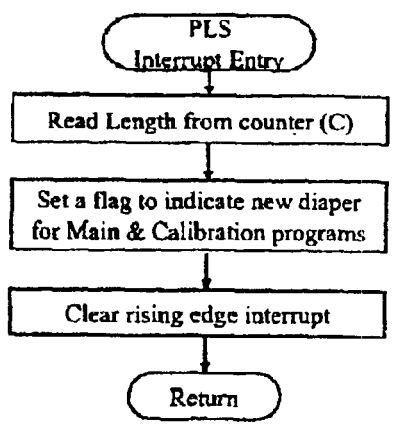

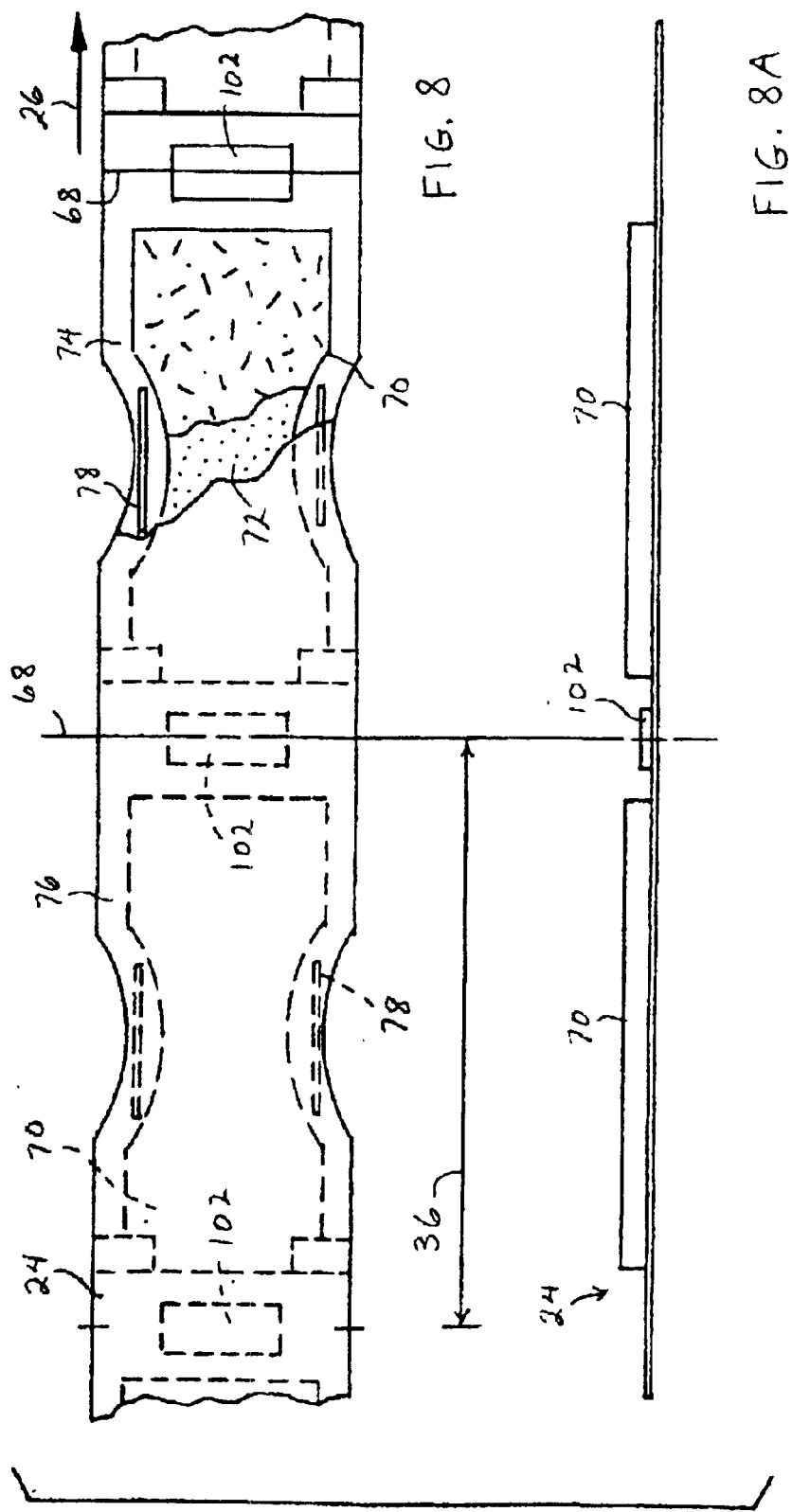

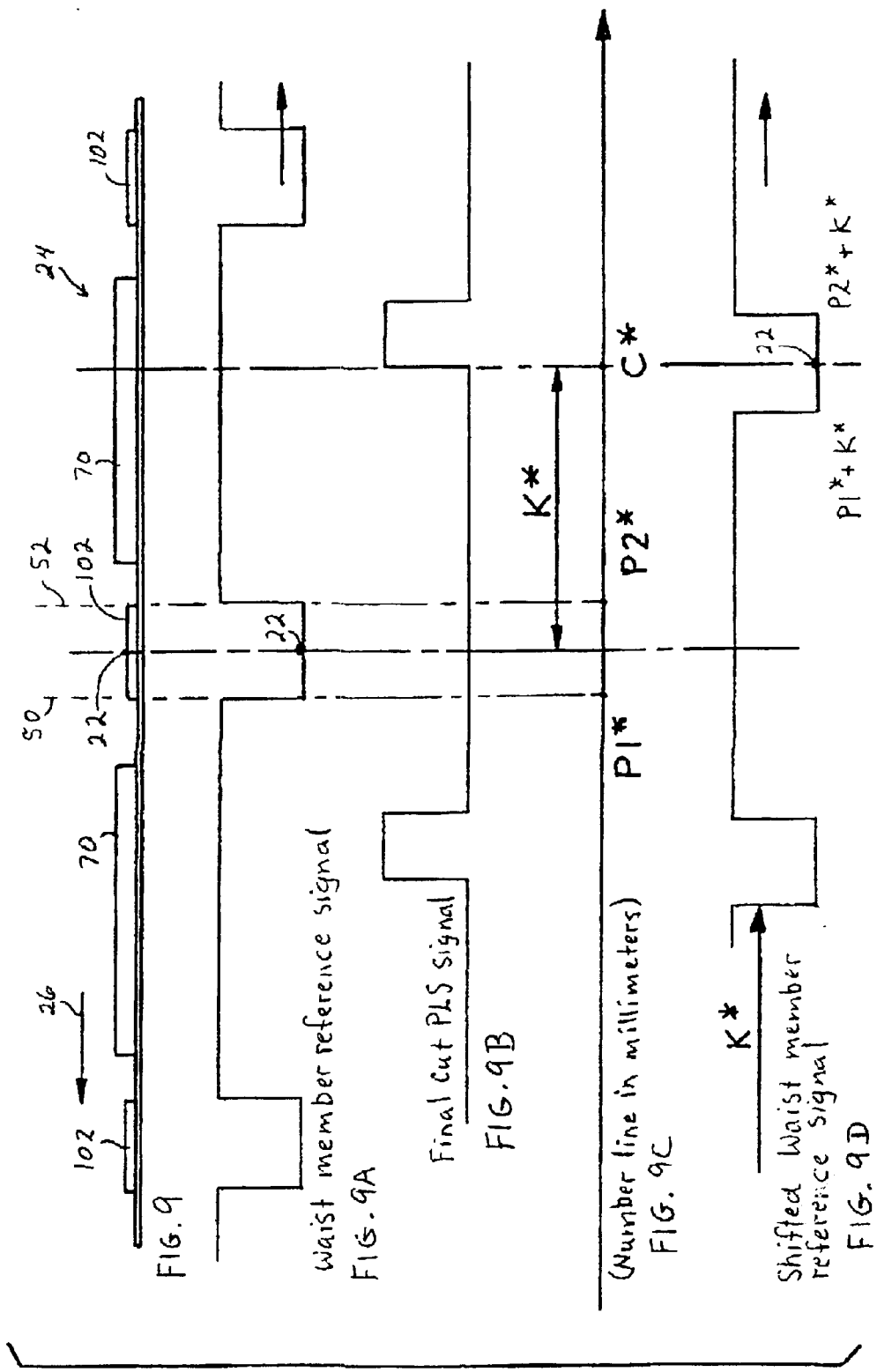

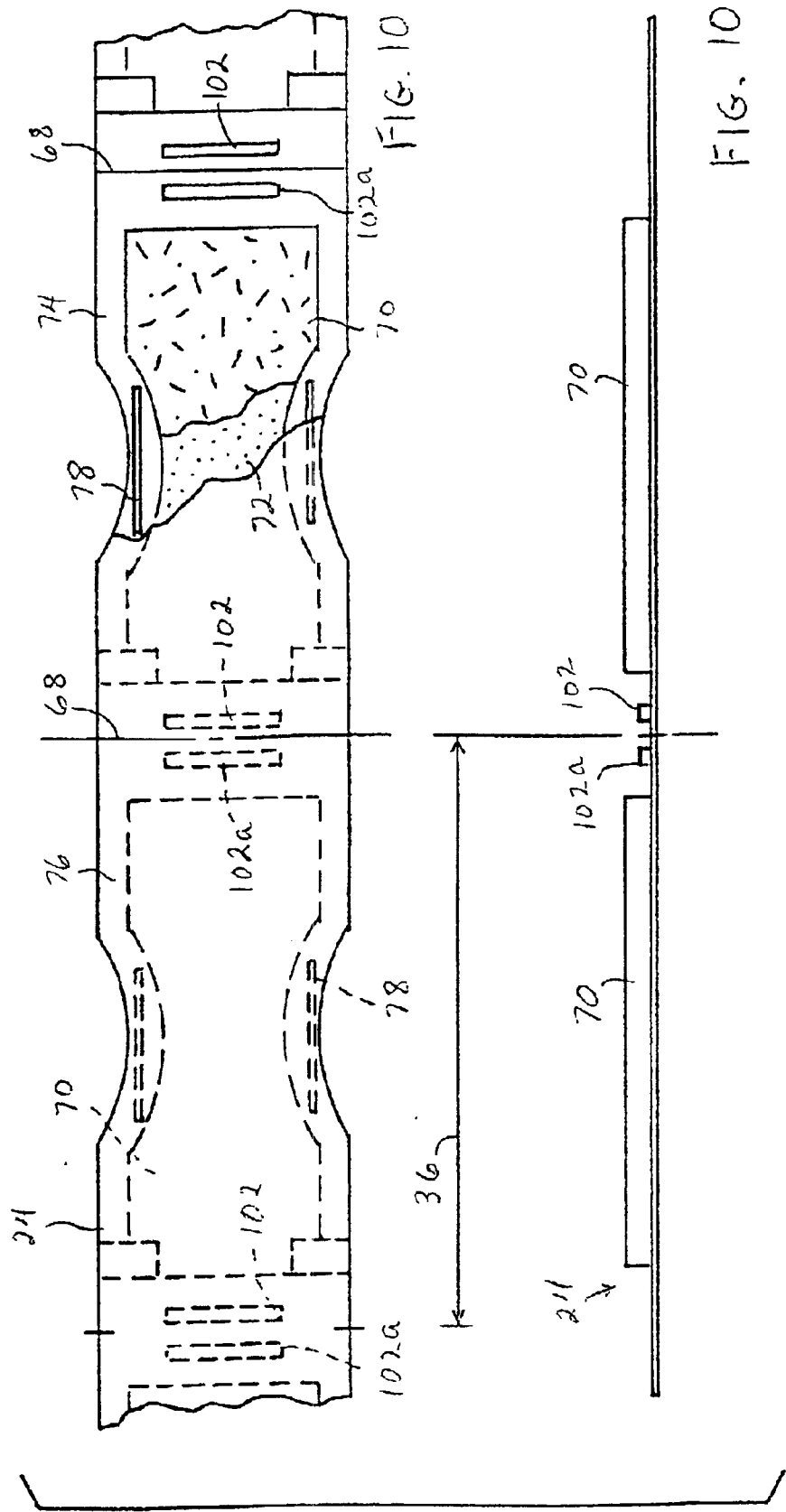

WEB VELOCITY-BASED REGISTRATION CONTROL SYSTEM

FIELD OF THE INVENTION

The present invention relates to a method and apparatus for inspecting a moving web, and controlling the locations of selected component elements. Additionally, the present invention can relate to a method and apparatus for controlling the locations and positioning the outcomes provided by selected processing operations.

BACKGROUND OF THE INVENTION

Conventional devices and systems have been employed for controlling the placement and positioning of selected components on a moving composite web, and for controlling selected processing operations, such as cutting operations. Such systems have been employed to produce absorbent articles, such as disposable diapers, adult incontinence products and feminine care products. The systems have typically tracked the moving web by using time-counts and encoder-counts.

Systems that incorporate electromagnetic radiation shifting indicia have also been employed. The indicia have provided signals which have been used in controlling various processes to be performed on the web, as well as for controlling movement of the web. The indicia have emitted wave-shifted electromagnetic radiation in response to incident radiation of a given range to provide a mechanism for determining the positioning of the web during movement as the processes are performed.

The registration inspection of composite articles during the fabrication of a series of such articles has been accomplished by making a two-dimensional image of a product and analyzing the image to determine the location of a component. The determined location has been compared to a desired location for the component in the composite article, and feedback control signals have been utilized to adjust the fabrication process so that the components will be at the desired locations in subsequent products. When a component is outside of its acceptable position, the article can be removed from the fabrication line without further processing.

Conventional devices and system, such as those described above, have not been sufficiently effective for inspecting the registration and location of component elements on a moving web. The systems have not been sufficiently able to control the registration of process operations and archive the registration data. Many imaging systems have been bulky and have been difficult to use in limited spaces. In addition, the conventional systems have not been sufficiently accurate, particularly when there have been extended distances between the locations of control sensors and the locations of their associated production operations. The systems have been susceptible to errors caused by various factors. Such factors can include, for example, slippage between the moving web and the processing equipment; non-uniform elongations in the web; length-wise oscillations in the web; and vertical vibrations in the web. As a result, poorly positioned or missing elements have still excessively degraded the quality of articles produced from the web, and poor-quality articles have not been efficiently or accurately culled and removed from the production lot. The conventional devices have also not been sufficiently able to automatically adjust the production process and machinery to keep desired parameters within acceptance specifications. As a result, production lines have suffered excessive downtime and reduced production efficiency.

BRIEF DESCRIPTION OF THE INVENTION

The present invention provides a method and apparatus for controlling a registration between a target point on a moving web, and a production outcome. A method aspect can include a transporting of the web along a movement direction past a reference detector, and a detecting of at least a first reference point on the web. At least the first reference point can be employed in a designating of the target point. The web can be transported past a speed-sensor, and the speed-sensor can measure a web speed of the moving web to provide web speed data. In a particular aspect, the web speed data can be integrated over time to determine a web-length which has been transported past the speed-sensor. The production outcome is actuated at a production-device, and in another aspect, the measuring of the web speed can include a substantially non-contact measuring of the web speed. In a further aspect, the actuating of the production outcome can be adjusted to occur after a reference-length of the web has been transported past the speed-sensor.

An apparatus aspect can include a transporter which can move the web along a movement direction past a reference detector. The reference detector can be configured to detect at least a first reference point on the web, and the first reference point can be employed in a designating of the target point. The web can be transported past a speed-sensor which is capable of measuring a web speed of the moving web to provide web speed data. In a particular aspect, an integrator can operate on the web speed data over time to determine a web-length which has been transported past the speed-sensor. A production device can be actuated to provide the production outcome. In another aspect, the speed-sensor can provide a substantially non-contact measuring of the web speed, and in a further aspect, a regulating system can adjust an actuating of the production outcome to occur after a reference-length of the web has been transported past the speed-sensor.

By incorporating its features and aspects in various operative arrangements and configurations, the present invention can more efficiently inspect a web moving at high speed to provide the desired, relative positional placements of selected production outcomes, such as the relative placements of components and the relative placements of processing operations. The locations of selected production outcomes can be arranged with improved accuracy, and the technique of the invention can provide greater versatility. The positional relationships between production outcomes can be better inspected, and desired registration data can be more effectively provided in convenient units, such as inches or millimeters. Additionally, the invention can provide an improved feedback control to maintain selected product and production parameters within desired ranges and specifications. The invention can better provide accurate, real-time information on each article during the production process, and individual, undesired articles can be more efficiently and more accurately identified for removal from a production lot. The quality of the production lot can be improved, and unnecessary waste can be reduced.

BRIEF DESCRIPTION OF THE DRAWINGS

The present invention will be more fully understood and further advantages will become apparent when reference is made to the following detailed description of the invention and the drawings, in which:

FIG. 3A shows a schematic representation of signals generated by a reference detector in response to a detection of the series of pads in the moving web illustrated in FIG. 3;

FIG. 3B shows a schematic representation of data or signals generated with respect to a selected production-device that has been configured to process the web representatively shown in FIG. 3;

FIG. 3C shows a schematic of a representative number line generated with respect to a position/speed-sensor that is observing the web illustrated in FIG. 3;

FIG. 3D shows a schematic representation of a shifted reference signal, where the reference detector signals illustrated in FIG. 3A have been shifted by a selected calibration factor;

FIG. 7 shows a representative flow chart that outlines the operation of a falling edge interrupt service routine that can be employed to detect and measure the first edge of the reference signal;

FIG. 7A shows a representative flow chart that outlines the operation of a rising edge interrupt service routine that can be employed to detect and measure the second edge of the reference signal;

FIG. 7B shows a representative flow chart that outlines the operation of interrupt serviced routine that can be employed to detect and measure the first or second edge of the production-device signal;

FIG. 8 shows a schematic, partially cut-away top view of a representative portion of a moving web which includes a waist member;

FIG. 8A a schematic, partial side view of a representative portion of the web illustrated in FIG. 8;

FIG. 9 shows a schematic, partial side view of a representative portion of a moving web which includes a series of pads with a waist member between pads;

FIG. 9A shows a schematic representation of signals generated by a reference detector in response to a detection of the web illustrated in FIG. 9 having the series of pads and a waist member between successive pads;

FIG. 9B shows a schematic representation of data or signals generated with respect to a selected production-device that has been configured to process the web illustrated in FIG. 9;

FIG. 9C shows a schematic of a representative number line generated with respect to a position/speed-sensor that is observing the web illustrated in FIG. 9;

FIG. 9D shows a schematic representation of a shifted reference signal, where the reference detector signals illustrated in FIG. 9A have been shifted by a selected calibration factor;

FIG. 10 shows a schematic, partially cut-away top view of a representative portion of an alternative moving web which includes a plurality of waist members;

FIG. 10A a schematic, partial side view of a representative portion of the web illustrated in FIG. 10.

DETAILED DESCRIPTION OF THE INVENTION

The present disclosure of the invention will be expressed in terms of its various components, elements, constructions, configurations, arrangements and other features that may also be individually or collectively be referenced by the term, "aspect(s)" of the invention, or other similar terms. It is contemplated that the various forms of the disclosed invention may incorporate one or more of its various features and aspects, and that such features and aspects may be employed in any desired, operative combination thereof.

It should also be noted that, when employed in the present disclosure, the terms "comprises", "comprising" and other derivatives from the root term "comprise" are intended to be open-ended terms that specify the presence of any stated features, elements, integers, steps, or components, and are not intended to preclude the presence or addition of one or more other features, elements, integers, steps, components, or groups thereof.

Figure 1:
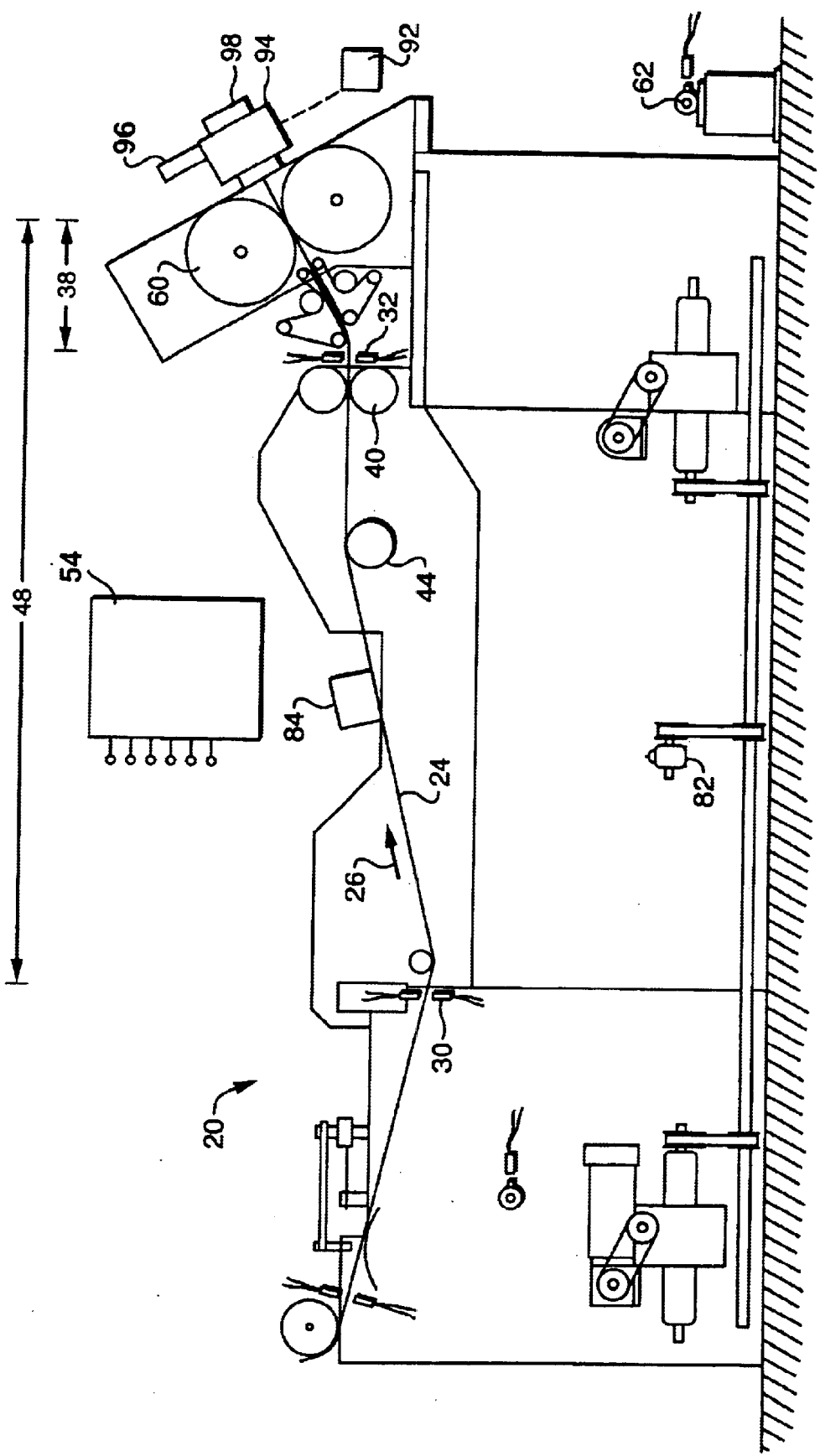
FIG. 1 shows a schematic, side view of a representative method and apparatus of the invention.
Figure 2:
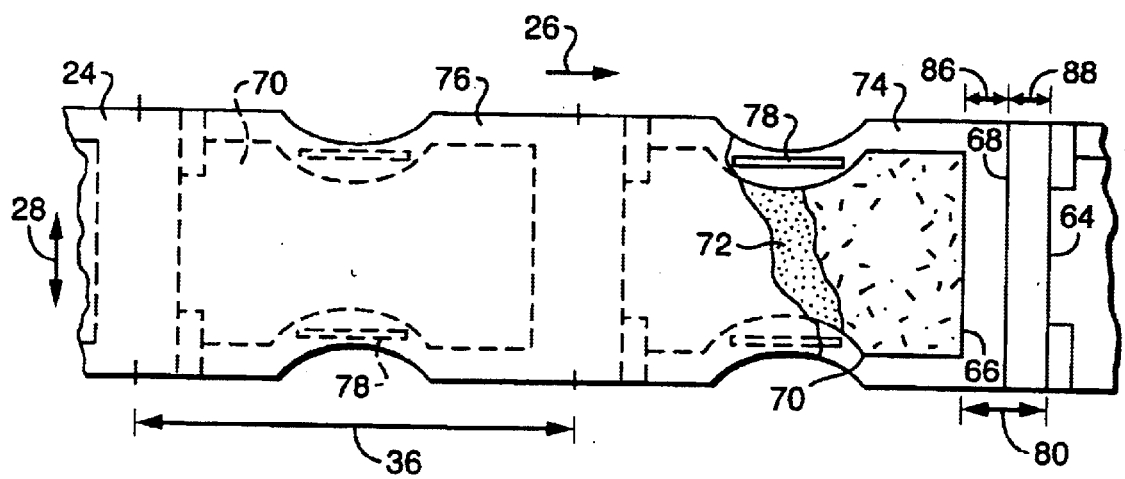
FIG. 2 representatively shows schematic, top view of a partially cut-away composite web that can be employed with the present invention.

With reference to FIGS. 1 and 2, the method and apparatus of the invention can have an appointed machine-direction or movement direction 26 which extends longitudinally, and an appointed cross-direction 28 which extends transversely. For the purposes of the present disclosure, the movement direction 26 is the direction along which a particular component or material is transported length-wise along and through a particular, local position of the apparatus and method. The cross-direction 28 lies generally within the plane of the material being transported through the method and apparatus, and is aligned perpendicular to the local movement direction 26. Accordingly, in the view of the arrangement representatively shown in FIG. 1, the cross-direction 28 extends perpendicular to the plane of the sheet of the drawing.

With reference to FIGS. 1 through 3D, the present invention can provide a distinctive method and apparatus 20 for controlling a selected registration between a target point 22 on a moving web 24, and a selected production outcome provided by a corresponding production operation. A method aspect can include a transporting of the web 24 along a longitudinal, machine-direction or movement direction 26 past a reference detector 30, and a detecting of at least a first reference point 50 on the web 24. The target point 22 can be designated by an employing of at least the first reference point 50. The web is transported past a speed-sensor 32, and the speed-sensor can measure a web speed of the moving web 24 to provide web speed data. In a desired feature, the speed-sensor can be configured to provide a substantially continuous output of the web speed data. In a further feature, the web speed data can be integrated with respect to the parameter of time to determine a web-length which has been transported past the speed-sensor 32. The production outcome can be selectively actuated, and in a particular aspect, the production outcome can be actuated at a selected production-device, such as provided by a cutter 60. In another feature, the measuring of said web speed can include a substantially non-contact measuring of the web speed, and in a further feature, the actuating of the production outcome can be adjusted to occur after a reference-length of the web 24 has been transported past the speed-sensor 32.

An apparatus aspect can include a transporter, such as provided by a system that includes transport rollers 44, which can move the web 24 along a movement direction 26 past a reference detector 30. The reference detector can be configured to detect at least a first reference point 50 on the web 24, and at least the first reference point can be employed in a designating of the target point 22. The web can be transported past a speed-sensor 32 which is capable of measuring a web speed of the moving web 24 to provide web speed data. In a desired feature, the speed-sensor can provide a substantially continuous output of the web speed data. In a further feature, an integrator function within the computer 54 can operate on the web speed data over the parameter of time to determine a web-length which has been transported past the speed-sensor 32. Additionally, a selected production-device, such as a cutter 60, can be actuated to provide the production outcome. In another feature, the speed-sensor can provide a substantially non-contact measuring of the web speed, and in a further feature, a regulating system can adjust an actuating of the production outcome to occur after a reference-length of the web 24 has been transported past the speed-sensor 32.

In a particular aspect, the invention can include a detecting of at least a second reference point 52 on the web 24. Another aspect of the invention can include a providing of at least one outcome signal or datum which operatively represents the actuating of the production outcome or the actuating of a selected production-device. In a further aspect, the invention can include a designating of a series of appointed articles or article lengths 36 along the moving web 24. Further features and aspects of the invention are set forth in the present disclosure.

By incorporating its features and aspects, alone or in combination, the various operative arrangements and configurations of the present invention can more efficiently inspect a web moving at high speed, and can more efficiently provide desired production outcomes. The production outcome can, for example, include a positional placement of a selected component, an occurrence of a selected processing operation, an adjustment of a processing operation, or the like. The technique of the invention can measure the positioning of selected production outcomes with improved accuracy, and can provide greater operational versatility. The positional relationships between production outcomes can be better inspected, and desired registration data can be more effectively provided in convenient units, such as inches or millimeters. Additionally, the invention can provide an improved feedback control to maintain selected product and production parameters within desired ranges and specifications. The invention can better provide accurate, real-time information on each article during the production process, and individual, undesired articles can be more efficiently and more accurately identified for removal from a production lot. The quality of the production lot can be improved, and unnecessary waste can be reduced.

It should be noted that the terms "data" and "signal" and derivatives thereof are to be interpreted in a general sense and are meant to designate various types of information produced during the operation of the invention. In particular, such types of information include, without limitation, information in the form of impulses or other modulations that can be mechanical, electronic, optical, electromagnetic or the like, as well as combinations thereof.

It should also be noted that the term "component" is intended to have a generalized meaning. Accordingly, the term may designate selectively processed regions, such as folded areas, cut edges and the like, as well as structural members, such as elastic strips, absorbent pads and the like, that may be employed to generate a web 24 or a selected article segment of the web. Although the following detailed description is made in the context of determining the relative placements of elastic strips and/or absorbent pads, it should be readily apparent that the method and apparatus of the invention can be employed to determine the relative locations of other components of the web 24, such as patches, tabs, tapes, adhesives, coatings, construction bonds or the like, as well as combinations thereof.

With regard to the present disclosure, the production outcome can be any desired result provided by a production operation or production-device. The production outcome can include any desired physical or chemical modification or adjustment of the web 24. For example, the production outcome may include an operational control or regulation of the web, a slowing down of the web, a speeding up of the web, a reorienting of the web, a repositioning of the web, a folding operation, a cutting operation, a shaping operation, a bonding operation, a pressing operation, an operational control or regulation of a production-device, a slowing down of a production-device, a speeding up of a production-device or the like, as well as combinations thereof. The production outcome may also include an application and/or assembly of a separately provided component or element onto the moving web 24. For example, the production outcome can include a continuous or intermittent coating operation, a continuous or intermittent application of adhesive, a placement of a patch of material, a thermal or other bonding operation, a separating operation or the like, as well as combinations thereof. The production outcome can be conducted or generated on the entire web, on portions of the web, or on specific components (e.g. a cutting of a surge management layer, or a leg opening area).

The present disclosure will be made in the context of a web comprising an interconnected plurality of absorbent articles, such as infant diapers, children's training pants, adult incontinence garments, feminine care articles, and the like. Such articles may be disposable articles that are typically discarded after limited use. It should be readily apparent, however, that the method and apparatus of the present invention may also be employed for the processing of other types of webs and articles.

As representatively shown in FIGS. 1 and 2, the web 24 can be employed to provide an interconnected plurality of disposable diaper articles. The web 24 can be a composite web which includes a substantially liquid impermeable layer 74, such as a breathable or non-breathable polymer film layer. For example, the layer 74 may be composed of polyethylene, polypropylene or the like, and may provide a composite which includes a nonwoven fabric. A plurality of separately provided, absorbent bodies, such as absorbent pads 70, can be superposed in facing relation with the layer 74. The pads 70 are typically composed of a cellulosic material, such as airlaid wood pulp fluff. The pads may also comprise a coform material composed of an airlaid mixture of cellulosic fibers and synthetic polymer fibers. In addition, the pads may optionally include natural or synthetic superabsorbent materials, such as pectin, carboxymethyl cellulose, guar gum, polysaccharides, crosslinked synthetic polymers and the like. For example, polymers composed of alkali metal salts of lightly crosslinked polyacrylic acid have been found to be suitable superabsorbent materials. Each pad 70 can also include a tissue wrap 72 to increase the pad structural integrity. The pads 70 are substantially regularly spaced along the machine-direction or movement-direction 26 of layer 74, and individual pads are separated by a discrete distance, such as provided by an end-seal length 80. Leg elastic members 78 are secured to layer 74 adjacent to lateral side edges of each pad 70. In addition, other components may be assembled to the web 24. For example, waist elastic members can be secured to layer the 74 adjacent to end edges 64 and 66 of the individual pads. A layer 76 of liquid permeable material, such as a spunbond nonwoven material, is superposed in facing relation with the pads 70 and the liquid impermeable layer 74. Thus, the pads 70 and other components may be sandwiched between the layers 74 and 76.

The various components of web 24 can be secured together by various suitable conventional techniques, such as adhesives, thermal bonding, sonic bonding or the like, as well as combinations thereof. For example, extruded lines, swirls or beads of adhesives are employed to secure the elastics to the liquid impermeable layer 74, and optionally, to the liquid permeable layer 76. Such adhesives can be hot melt adhesives, pressure-sensitive adhesives or the like, as well as combinations thereof. If desired, the adhesives may also be applied by conventional spray techniques. Similarly, adhesives can be employed to bond either or both of the layers 74 and 76 to the pad 70.

Desirably, the side margins and side edges of the web 24 are contoured by removing selected sections. For example, a conventional cutting mechanism, such as a die cutter or water cutter, can be employed to cut away selected portions of the web side margins to provide appointed the leg openings of individual diaper articles.

It has been desirable to accurately inspect the web 24 to assure a uniform quality of the individual articles formed from the web. The web 24 must be rapidly examined for missing components and for misplaced or misaligned components. Of particular interest may be the relative placement between individual pads 70, the relative placement of other components, and/or the relative placement of a separation line 68 between the pads to provide individual articles. For example, the length of material between an individual end edge 64 or 66 and the separation line 68 may be too long or too short. If a parameter does not meet its predetermined acceptance criteria, it is desirable to identify and remove the individual out-of-specification diaper from the production lot. It is also desirable to automatically adjust the production process and apparatus to bring all parameters within accepted specification ranges. The distinctive apparatus and method of the present invention can advantageously improve the accuracy of the inspection, measurement and control of sequential process operations, and can more effectively control the quality of the produced articles.

With reference to FIGS. 1 through 3D, the method and apparatus of the invention can be configured to provide an improved system for determining and controlling the front and back end-seal lengths of an article, such as a disposable diaper. In each article, the front and back end-seal lengths are distances between the edges of the absorbent pad and the terminal, cut edges of the article. As illustrated, a diaper web has been assembled with all of its components (equipment not shown), and the web 24 is ready for a final cutoff operation that separates the web into individual articles for packaging. The selected transporter system is operatively configured to advance the web 24 along the appointed movement direction 26. It should readily be appreciated that the transporter can be any operative transporting mechanism or system. Suitable systems can, for example, include rollers, belts, screens, pneumatic conveyors, electromagnetic conveyors and the like, as well as combinations thereof. In the representatively shown arrangement, the transporter can be provided by a system which includes transporter rollers 44.

It should also be readily appreciated that the various sensors and detectors employed with the present invention can be provided by any operative detecting device. Suitable devices can, for example, include mechanical detectors, electromagnetic detectors, optical detectors, ultraviolet detectors, infrared detectors, x-ray detectors, particle beam detectors, lasers, vision imaging sensors or the like, as well as combinations thereof.

As representatively shown, the actuating of the production outcome can include a separating of the moving web 24 with an operative cutting device 60. Any suitable cutting mechanism or system may be employed. Suitable cutting systems can, for example, include oscillating knives, rotary knives, die cutters, water cutters, laser cutters, particle beam cutters, or the like, as well as combinations thereof.

The reference detector 30, such as provided by an optical scanner (e.g. photo-eye), can detect the pads and end-seal areas that are to be cut. A task-signaling device, such as provided by a programmable limit switch (PLS) 62, can be mounted on the drive mechanism or otherwise operatively connected to the cutoff device 60 to indicate the relative position of the final cut. A position/speed-sensor 32 is mounted between the photo-eye and the diaper cutoff device to determine when a selected amount or length of web has traveled past the speed-sensor. The selected web length is correlated to a distance that separates the photo eye and the cutoff device. All the signals are connected to the computer to conduct various functions and operations, such as estimating the end-seal length, inspecting the product to ensure quality, controlling the cutting position, recalibrating the control system if the set-point drifts, storing data and retrieving the data for further analysis when needed.

The method and apparatus of the invention may include a system of time counts or a system of encoder counts for tracking the positions of selected components on a moving web. Examples of techniques which employ various arrangements of encoders and encoder counts are described in U.S. Pat. No. 4,837,715 entitled METHOD AND APPARATUS FOR DETECTING THE PLACEMENT OF COMPONENTS ON ABSORBENT ARTICLES by T. Ungpiyakul et al., which was issued Jun. 6, 1989 and in U.S. Pat. No. 5,235,515 entitled METHOD AND APPARATUS FOR CONTROLLING THE CUTTING AND PLACEMENT OF COMPONENTS ON A MOVING SUBSTRATE, AND ARTICLE MADE THEREWITH by T. Ungpiyakul et al., which was issued Aug. 24, 1993. The entire disclosures of these documents are incorporated herein by reference in a manner that is consistent herewith.

Figure 4:
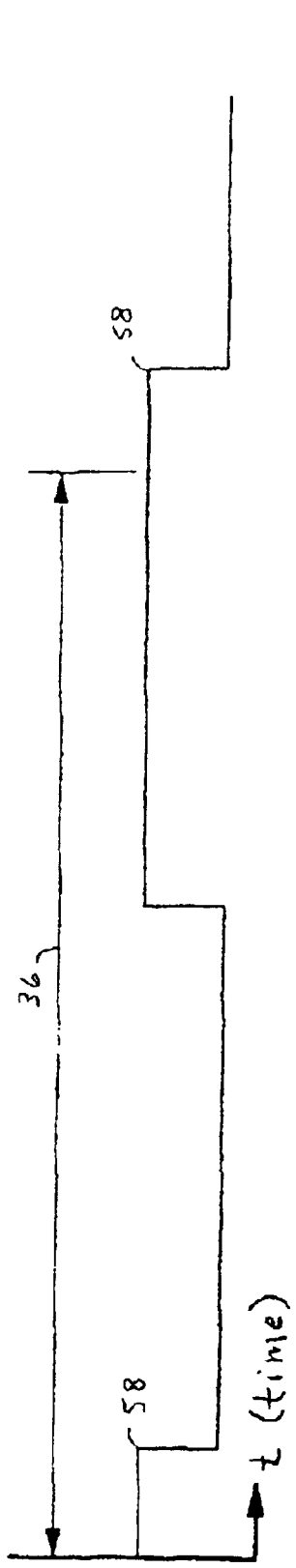
FIG. 4 shows a representative marker pulse that can be generated once for each appointed article or article length.

The method and apparatus of the invention can include a mechanism for providing marking data. The marking data can, for example, be configured as electronic pulses or signals, and the data can correspond to the position and presence of an individual, selected article or article length 36. The marking data can also correspond to a particular position and phasing of the component elements of the invention relative to each other and relative to the web 24. The marker data can have the form of electrical or electronic impulse signals, as representatively shown in FIG. 4. Additionally, the method and apparatus can provide at least one marker pulse 58 (and desirably, a series of marker pulses) which can be employed to obtain the phase relationship between the various electrical signals and the mechanical elements of the apparatus. One marker pulse 58 can be generated for each article or article length comprising the web 24. The marker pulse may, for example, be configured to occur one time per revolution of a line shaft of the process or apparatus. In another arrangement, the marker pulse may be derived from the signals produced by the reference detector 30. Electrical signals that correspond to the marker pulses can be routed through suitable electrical conductors, such as conductors S32, to an operative computerized processing unit 54 (e.g. FIGS. 1 and 1A). Such computers and processing units are conventional and well known.

A line shaft encoder 82 can be connected to a main line shaft of the manufacturing equipment, and the line shaft can be connected to a conventional drive mechanism (not shown) that is operatively configured to move a conventional conveyor to transport the web 24 through the process and apparatus. Desirably, the connection can be through an adjustable ratio gear box which can be selectively controlled such that one encoder shaft revolution substantially corresponds to one article-length of the moving web.

Figure 1A:
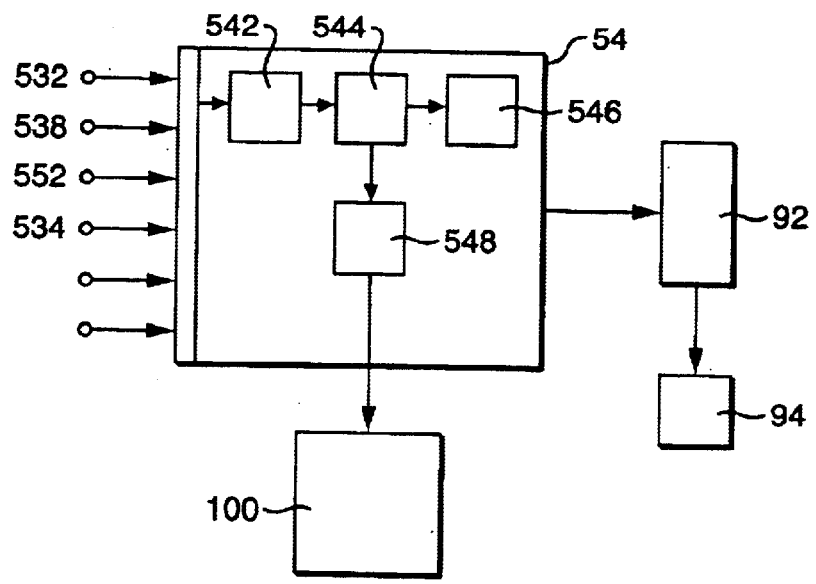
FIG. 1A a schematic representation of a computer system that can be employed with the invention.
Figure 4A:
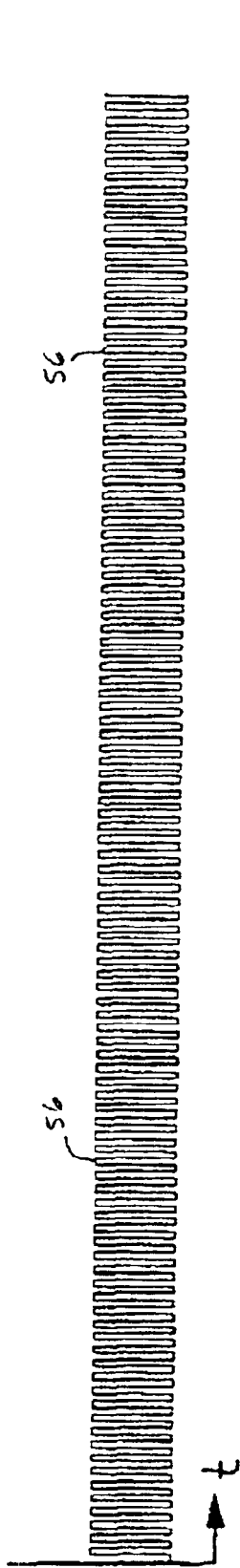
FIG. 4A shows a representative signal pattern as generated by an encoder.
Figure 4B:
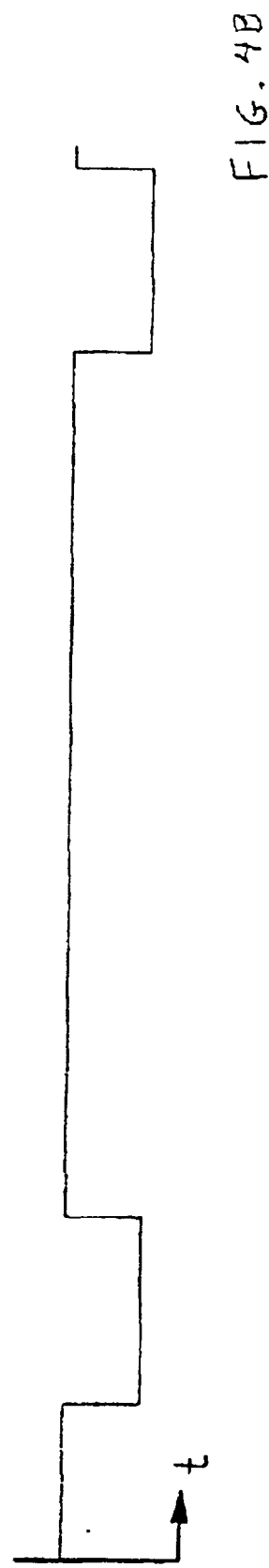
FIG. 4B shows a representative signal generated by a proximity switch or programmable limit switch employed on a selected process function device.

A portion of the line shaft encoder 82 can further provide a metering mechanism for generating substantially regularly occurring phasing pulses 56 (FIG. 4A). The shown configuration of the invention can, for example, generate approximately 2000 phasing pulses per shaft revolution, and thus, 2000 pulses per diaper article. These pulses can be employed as a "ruler" to measure the phase and position relationships between the various electrical signals generated by the apparatus of the invention, and can be employed to develop desired measurements of the distances between selected components of web 24. In the shown configuration of the invention, the phasing pulses are in the form of electrical signals, which are suitably directed to the computer processing unit 54 through appropriate electrical conductors S38 (FIG. 1A).

Various suitable reference points on web 24 can be employed with the method and apparatus of the invention. For example, convenient, periodically occurring reference points are the longitudinally located end edges 64 and 66 of each of the individual pads 70. As representatively shown in FIG. 2, the end edges can extend transversely along the cross-direction 28 of the web 24.

The reference detector 30, such as provided by a photo-eye (PE) detector, observes the web 24 as it passes by the location of the reference detector. Where the reference detector 30 is a photo-eye or other optical detector, an operative optical contrast between selected components of the web can be employed to identify the locations of those components. For example, due to an optical contrast between the web portions containing the pads 70 and the web portions between the pads, the photo-eye detector can generate an electrical signal pulse corresponding to trailing pad edge 64 and a leading pad edge 66. The selected electrical signal pulses can be directed to the computer processor 54 through suitable wiring S34 (e.g. FIG. 1A).

In some situations, the web components may not be readily detected by conventional optical detectors, such as photoelectric detectors, because of insufficient contrast between the selected components and the remainder of the web. For example, the liner 76 may cover and obscure the edges of the pads. To address this situation, selected components may be treated with a brightening component, such as an optical brightener. Suitable optical brighteners include, for example, UVITEX O.B. manufactured by Ciba Geigy, and LEUCOPURE EGM manufactured by Sandoz Chemicals Corporation. Other suitable optical brighteners include INTRAWITE O.B. manufactured by Crompton and Knowles, and PHORWITE K2002 manufactured by Mobay Chemical Company.

In particular arrangements of the invention, the optical brightener can be sensitive to ultraviolet (UV) radiation. The optical brightener can, for example, be capable of absorbing UV radiation and then fluorescing to emit visible light spectra that can be sensed by an optical detector. For the purposes of the present description, UV radiation is intended to designate electromagnetic radiation having wavelengths within the range of about 20–400 nm. In a preferred arrangement, the reference detector 30 may be provided by a UV-activated detector, such as a SICK detector model LUT14 available from Sick Optik Elektronik, Inc. located in St. Paul, Minn.

In the various configurations of the method and apparatus of the invention, the computer 54 can be any computer that can be suitably programmed and otherwise configured to operate the method and apparatus of the invention. In the shown configuration, for example, the computer 54 can be a VME system comprising a Motorola MVME-172 CPU board, a VMIC 6016, serial I/O board, and one VMIC 1181 32 I/O board. The Motorola components are available from Motorola Computer Group, Tempe, Ariz., and the VMIC components are available from VME Microsystems International Corporation, Huntsville, Ala.

As representatively shown in FIG. 1A, the computer 54 can include a comparator mechanism or system 544 which can receive spacing data generated by an evaluating mechanism or system 542. The spacing data can correspond to or otherwise represent a spatial distance between a selected reference point, and a selected component or production outcome. In a particular arrangement, for example, the evaluating system 542 can be configured to generate spacing data by operatively subtracting the encoder position of the component or production outcome from the encoder position of the selected reference point.

The comparator system can compare the spacing data with a predetermined acceptance spacing range, and if the spacing data is outside the acceptance range, the comparator system can send an appropriate reject signal to a computer culling mechanism or system 546. In addition, the computer comparator 544 can send appropriate signals to a registration control loop 548 for a selected component. The output from the control loop can be routed to a suitable regulating mechanism or system 100 for adjusting the operation and phasing of an applicator or other production-device which places the selected component onto the moving web 24.

With the shown configuration of the invention, the culling mechanism can also be connected to include a programmable controller 92 and a diverter mechanism 94. The programmable controller can receive instruction signals from the computer 54, which identify defective articles. The controller can employ the data to suitably direct the diverter 94 to selectively route individual articles to either a cull chute 96 or an acceptance conveyor 98. Articles sent through the cull chute are discarded, and articles sent along the acceptance conveyor are routed for further processing, such as folding and packaging.

In the manufacture of disposable diaper articles, the relative positions and distances between the pads may be important. In particular arrangements, the relative positions between the pads and other components, such as waist elastic members, may be important. The method and apparatus of the present invention may be configured to inspect the relative locations of the selected components. To accomplish this, the speed-sensor 32 can be configured to provide position data corresponding to the location of the selected components on the moving web 24. For example, the speed-sensor 32 can be employed to generate position data corresponding to the pads 70, and the position data may be further employed to identify and designate at least one target location or other target point 22 that is positioned between consecutively-occurring pads.

Referring to FIG. 1, the reference detector 30 can be suitably positioned adjacent the web 24. Various devices can be employed as the reference detector. Suitable devices can include, for example, a remote amplifier module PS2-61, in conjunction with PS-56 photoelectric sensors are available from Keyence Corporation Of America, a business having offices located in Woodcliff Lake, N.J. 07675; or an AMCI 1731 device that is available from Advanced Micro Controls, Incorporated, a business having offices located in Terryville, Conn. 06786.

As the web 24 passes by the detector 30, the reference detector can sense selected edges. The edges can, for example, correspond to the trailing end edge 64 of a first pad and the leading end edge 66 of a next successive, consecutively following pad. The reference detector 30 generates corresponding electrical signals and passes them to the computer 54 through a suitable coupling, such as conductive wiring. The number of phasing pulses which are detected between the edges sensed by the reference detector 30 can provide desired position data corresponding to the relative locations between selected components, such as the relative the relative locations between the pad edges 64 and 66. The number of encoder phasing pulses (e.g. FIG. 4A) that occur between the sensing of the pad edges can be replaced or supplemented with position data that is derived from the speed-sensor 32.

For pad detection, the photo-eye or other reference detector may be configured such that as the web passes the detector, the state of the corresponding output signal can be "high" where the absorbent pad is present and blocks the photo eye optical beam. Additionally, the state of the output signal can be "low" where the pad is absent and the web provides the end-seal area. Alternatively, the photo eye can be configured in such that the signal state is "low" when the beam absorbent pad is present, and the signal state is "high" when the pad is absent. This detector signal is illustrated in FIG. 3A, and is connected to a computer than can promptly and accurately scan the signal transitions from "high" to "low", and "low" to "high".

Accordingly, the reference detector 30 can provide operative reference data, and the reference data can correspond to the leading and trailing edges of individual pads 70. In such a configuration of the invention, the pads 70 are desirably constructed and arranged to be detectable by irradiation with light. For example, a tissue wrap 72 extending over each pad 70 can be treated with a suitable optical brightener, such as the optical brighteners previously discussed. With such an arrangement, it is important that tissue wrap 72 extend closely proximate to the machine-directional, end edges 64 and 66 of the pads 70 to ensure an accurate identification and designation of these pad edges. Thus, the reference detector 30 can be employed to generate information and data which correspond to the positions of selected components, such as the end edges of the pad or the edges of the waist elastic members.

A task-signaling device is employed to provide function-data that operatively identifies and designates the occurrence of a selected production outcome. Desirably, the function-data can identify each occurrence of the selected production outcome, and can identify each operation of the production-device employed to generate the selected production outcome.

The task-signaling device may, for example, include a programmable limit switch (PLS) 62. Suitable programmable limit switches include, for example, a GEMCO 1771-PLSB1 device available from Patriot Sensors and Controls Corporation, a business having offices in Clawson, Mich. 48017-1097; or a device such as the AMCI 1731 which is available from Advanced Micro Controls, Incorporated, a business having offices located in Terryville, Conn. 06786.

The programmable limit switch 62 can be operatively coupled with a selected production-device, such as a separating mechanism for dividing the web 24 into individual article lengths or articles 36. For example, the programmable limit switch may be belt-connected, geared or otherwise connected to the main line shaft of the manufacturing equipment. As representatively shown in FIG. 1, the separating mechanism can be provided by a system that includes a rotary cutter 60 or other operative cutting device. The PLS can generate a pulse signal corresponding to each time that the cutter separates the web, and the signals can be routed to the computer 54 through suitable conductors S52 (e.g. FIG. 1A). The occurrence of the PLS signal may or may not correspond exactly with the occurrence of the actual cutting operation. As a result, an adjustment factor can be provided to the computer 54 to allow an accurate determination of the precise position of the cutting line 68 relative to other components of the web 24.

The reference detector 30 is desirably located as close as possible to the cutter 60 or other selected production-device to reduce measurement errors caused by any slipping, stretching or contracting of the web 24 that might occur between the time that the reference detector 30 observes the web and the occurrence of the selected production operation. The desired arrangements, however, have often been difficult to obtain. In the shown configuration, for example, the side margins of the web 24 may be processed by a folding mechanism 84, and may be folded over toward the longitudinal centerline of the web prior to the cutting operation. Portions of the folded side margins can obscure and cover various components, such as the pads and the waist elastic members. As a result, a placement of the reference detector 30 proximate the cutter 60 would impair the operation of the reference detector. Accordingly, the reference detector 30 has been spaced a longer distance away from the cutter 60.

In a particular aspect, the configuration of the invention can better accommodate a spacing of the reference detector 30 away from the cutter 60 or other production-device by a relatively large production-device distance 48. In a particular aspect, the production-device distance can be down to a minimum of about 1 meter (1 m), or less. The production-device distance can alternatively be at least about 2 m, and optionally, can be at least about 3 m to accommodate the positioning of desired, intervening equipment and processing operations. In other aspects, the production-device distance can be up to a maximum of about 10 m, or more. The production-device distance can alternatively be not more than about 7 m, and optionally, can be not more than about 5 m to provide improved performance. In a further feature, the production-device distance can be at least about 20 cm, and can alternatively be at least about 30 cm. In still another feature, the production-device distance can be not more than about 100 cm, and can alternatively be not more than about 80 cm. In a desired arrangement, for example, the production-device distance can be about 50 cm.

Since the moving web 24 can undergo variations in stretch or changes in machine-directional length due to slipping, stretching and contracting of the moving web, a second detector, such as a second photo-eye, has been employed to provide additional reference data corresponding to selected components. For example, the second photo-eye has been configured to provide additional data pertaining to the end edges of the pads 70. In particular arrangements, the second photo-eye has been located closely adjacent to the position at which the web 24 is cut or otherwise separated into individual diaper articles. At such a position, the second photo-eye can sense the leading and trailing end edges of pads 70 and provide more accurate, updated reference data corresponding to the selected component.

With regard to the present invention, the accuracy and efficiency of the method and apparatus can be improved by employing the speed-sensor 32. The speed-sensor can better accommodate a placement that is located more closely proximate to the position of a desired production operation or outcome, and can better accommodate a placement that is located more closely proximate to the corresponding production-device. In the representatively shown configuration, for example, the speed-sensor 32 can be located closely adjacent to the cutter device 60 which cuts or otherwise separates the web 24 into individual articles or article lengths.

With reference to FIG. 1, the invention can include a spacing of the speed-sensor 32 away from the cutter 60 or other selected production-device by a selected offset distance 38. In a particular feature, the offset distance 38 can be a minimum of about 0.1 meter, or less. In another feature the offset distance can be up to a maximum of not more than about 5 meters, and can alternatively be not more than about 1 meter. If the offset distance is outside the desired values, there can be excessive operational errors caused by slippage between the moving web and the processing equipment, non-uniform elongations in the web, length-wise oscillations in the web, vertical vibrations in the web, or other such disturbances.

The speed sensor is operatively positioned relative to the web to provide accurate information to the process control system. In a particular feature, the speed sensor 32 can have a selected spacing distance away from the web 24, and the spacing distance can be not more than a maximum of about 500 cm. In a desired arrangement, the spacing distance can be approximately 10 cm. Where the speed sensor employs one or more measurement beams (e.g. one or more laser beams), the sensor beam system is configured and arranged to provide an operative measurement of the speed of the moving web 24.

In a particular arrangement, the speed sensor can be positioned to provide an operative angle incidence between the beam direction and the travel path of the moving web at the location of the speed sensor. The desired angle of incidence between speed sensor beam and the web will depend upon the particular characteristics of the selected speed sensor. For example, the speed sensor beam may be arranged substantially perpendicular to the travel path of the moving web 24. In desired configurations of the invention, the speed sensor are supported with a firm, low-vibration mounting, and any lenses are kept clean and substantially free of excessive occlusions.

The speed of the moving web should be maintained within the operative range of the speed sensor. In a particular aspect, the web speed can be at least a minimum of about 30 ft/min (about 9.14 m/min). In another aspect, the web speed can be not more than a maximum of about to 3000 ft/min (about 914 m/min).

A further feature of the invention can include a stabilizing of the web 24 at a web-control mechanism 40. Various conventional web-control mechanisms may be employed. Such web-control mechanisms can, for example, include vacuum conveyors, feed belts, cooperating nip rolls, s-wrap systems, or the like, as well as combinations thereof. The web-control mechanism can provide a more uniform feed of material past the speed sensor, can reduce any horizontal or vertical bouncing of the web, and can provide for a more stable presentation of the web 24 to the speed sensor 32. With reference to FIG. 1, the web-control mechanism 40 can, for example, be provided by a mechanism which includes the illustrated system of counter-rotating nip rollers.

To provide improved effectiveness, a desired feature of the invention can have the web-control mechanism arranged at a location which is proximate the speed sensor 32. In a particular arrangement the web-control mechanism can be substantially, immediately adjacent the speed sensor. In other arrangements, a separation distance between the web-control mechanism 40 and the speed sensor 32 can be about 0.5 meter. In a further aspect, the separation distance between the web-control mechanism and the speed sensor can be not more than a maximum of about 1 meter. If the separation distance is outside the desired values, the benefits of the invention can be reduced due to undesired, intervening influences, such as variations in the web speed, variations in the vertical positioning of the web, variations in the horizontal positioning of the web, or the like.

In a particular aspect, the measuring of the web speed can employ a substantially non-contact measuring device or process. With a particular feature of the substantially non-contact measuring system, there is substantially no mechanical contact between the measuring device and the moving web 24. Accordingly, there can be substantially no direct or indirect, mechanical inter-engagement between the speed-measuring device and moving web. As a result, the speed-sensor can be less susceptible to errors caused by perturbations, such as mechanical slippage between the web and the speed-measuring mechanism, web stretching and/or contracting, web bouncing, web vibration, or the like, as well as combinations thereof. The method and apparatus which incorporates the speed sensor can also better self-correct or otherwise compensate for such perturbations. In a desired configuration, the speed sensor 32 and the measuring of the web speed can be configured to employ a Doppler-related measurement. In another aspect, the speed sensor and the determining of the web speed can employ a Doppler-related measurement produced with one or more lasers. For example, the Doppler-related measurement may employ a technique referred to as "laser Doppler velocimetry".

In desired aspects, the reference detector 30 and the speed-sensor 32 can cooperate to provide a particularly effective mechanism for providing reference data that corresponds to the selected reference points on the moving web 24. An associated evaluating mechanism, such as provided by an operative portion of the computer 54, can process the data from the speed-sensor 32 to more accurately determine and identify the desired target location on the web 24, and to more accurately position the selected production outcome at the target location. For example, the method and apparatus of the invention can more accurately place the separation line 68 relative to the other components of the web. In particular arrangements, the method and apparatus can more accurately position of the separation line between consecutive pads.

The speed-sensor can desirably be positioned in the process between the reference detector 30 and the cutoff device 60, and can be employed to derive a number line 90. The number line can then be employed to determine relative positions of web components, production-operations and production-outcomes.

In the various configurations of the method and apparatus of the invention, a variety of speed-sensor devices may be employed. For example, suitable speed-sensors can include a SENSORLINE DANTEC 7520 which is available from Dantec Measurement Technologies, a business having offices located at Mahwah, N.J., U.S.A.; a TSI LS200 which is available from TSI Incorporated, a business having offices located at St. Paul, Minn., U.S.A.; a TSI LS50M MULTI-PLEXED LASER SPEED system, available from TSI Incorporated; or a SPEEDREADER Model SR-110 which is available from LightWorks LLC, a business having offices in Berthoud, Colo., U.S.A. Another suitable speed-sensor can include the SENSORLINE system, which is available from DANTEC Measurement Technology, a business having offices located in Skovlunde, Denmark.

The speed-sensor can be operatively configured to provide improved information to the computer 54 in the form of web position (travel) data. Such data can be expressed in any operative unit of measure. In the representatively shown configuration, for example, the data can be expressed in units of length, such as millimeters. The speed-sensor 32 can, for example, be employed to generate a more accurate number line 90 (e.g. FIG. 3C), and the values of the number line can be operatively counted or integrated to provide a more accurate and more efficient operation the method and apparatus of the invention. In a particular arrangement, the speed-sensor can be configured to generate corresponding electrical signals and pass them to the computer 54 through an operative coupling, such as through conductors S38.

As representatively shown, the programmable limit switch (PLS) or other task-signaling device may be operatively connected to the drive mechanism for the cutoff device 60. The PLS can be configured to produce a pulse that changes state from low to high at the selected period, such as a period of once per article, to indicate a relative position of the final cutting along the appointed separation line 68 (e.g. FIG. 2). For increased accuracy, the timing of the PLS pulse can be programmed to occur near but before the actual cutting operation.

The various sensors and detectors employed in the present invention can provide data for process control. Such data can include data regarding the positions of product components, data regarding the positions of the operating machine mechanisms, and data regarding the web speed data. The web speed data can be suitably correlated with the physical and "dynamic" distances between sensors and the mechanisms of the operating equipment. For example, in a simple first case of two sensors that are spaced apart with nothing between them, the physical distance is the distance from a theoretical sensing edge of the first sensor to a theoretical sensing edge of the second sensor. In another case where the two sensors are at the same locations along the web path, but the gain of one (or both) sensor(s) can be adjusted to provide a difference between the signal-edge from the first sensor and the signal-edge from the second sensor. If the movement of the web changes, for example, due to vibration or a change in web elongation, the difference between the two signal-edges can also change. The change in the difference between the two signal-edges is the "dynamic distance". The dynamic distance can vary even when the physical distance is constant.

Figure 3:
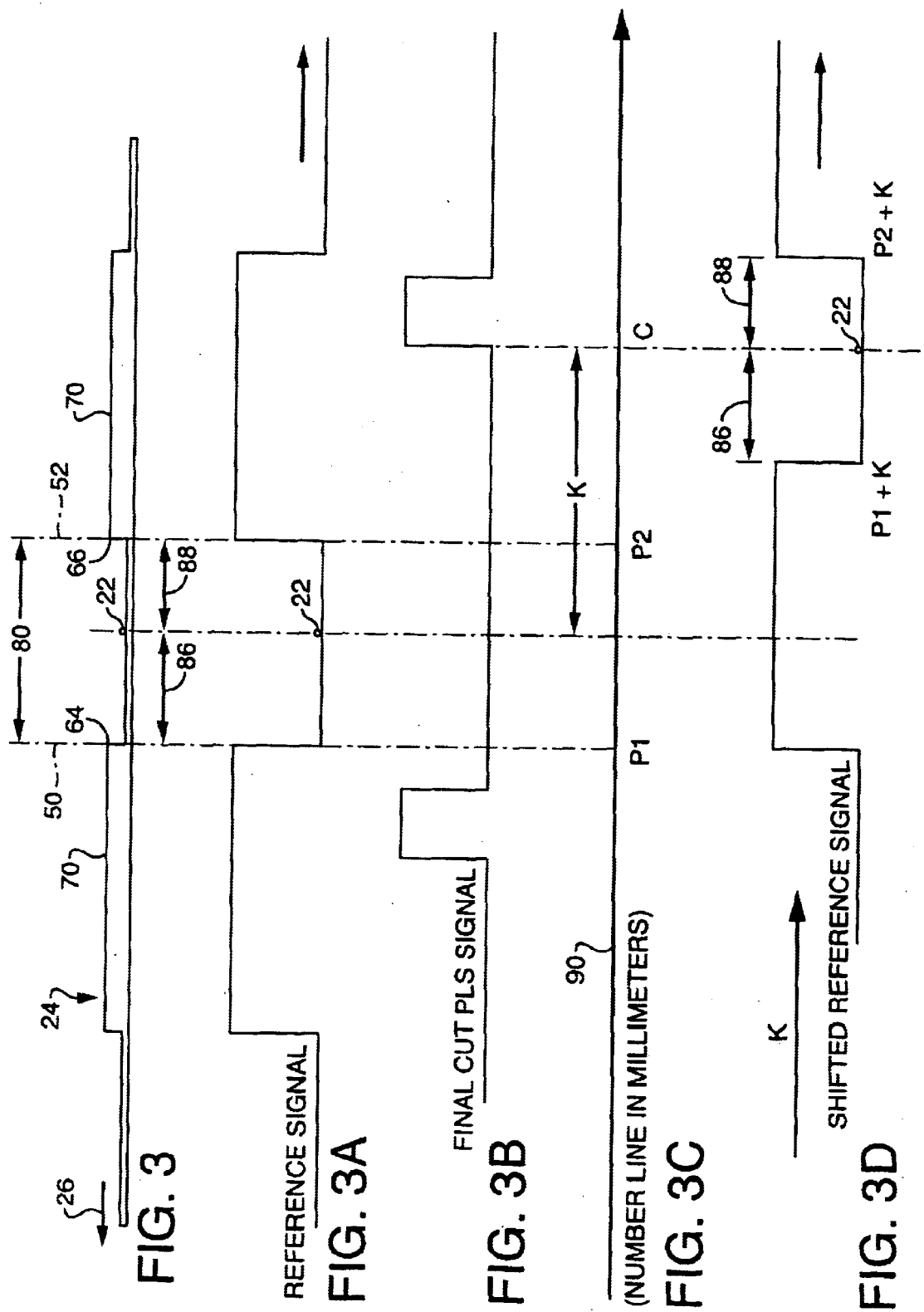
FIG. 3 shows a schematic, partial side view of a representative portion of a moving web having a series of individual pads.

FIG. 3 shows a schematic representation of a composite web having a series of separate, space-apart pads 70. FIG. 3A shows a representative schematic of corresponding signal pulses that can be generated by the reference detector 30 as the reference detector observes the moving web.

FIG. 3B shows a schematic of representative signals that can be generated by the selected task-signaling device, such as the programmable limit switch 62. The programmable limit switch signal can, for example, be generated each time the cutter 60 operates to divide the web into individual articles, but the switch signals may not exactly coincide with the actual cutting operations. The actual cutting may occur at a certain number of phasing pulses before or after the generation of the programmable limit switch signal. To compensate for this factor, the computer 54 can be empirically calibrated to selectively offset or shift the programmable limit switch signal by a selected amount. For example, the limit switch signal may be offset by a selected number of encoder phasing pulses, or by a selected number-line units derived from the speed-sensor 32. As a result, the shifted programmable limit switch data can substantially corresponds to the actual location of the separation line 68 relative to the other components of the web. Accordingly, the offset of the function-data from the task-signaling device can be selectively adjusted to ensure that the computer 54 is provided accurate data regarding the actual occurrence of a selected production outcome, such as the cutting of the web.

FIG. 3C schematically shows a representative number line 90 that can be generated by employing the speed-sensor 32. The number line can provide gauge data for the invention, and can be expressed in any convenient units. In desired aspects, the number line 90 can be the result of an integration of the speed sensor output over time to provide measurements in units of length, such as inches, millimeters, or the like.

In a desired aspect of the invention, the adjusting of the actuating of the production outcome can include a regulating of the reference-length by employing a calibration factor "K" (e.g. FIG. 3B). The reference-length can, for example, be the amount of web length that is ordinarily present between the reference detector 30 and the selected production-device (e.g. cutter 60). Additionally, the reference-length can be the amount of web length that has been measured as having been delivered or transported past the speed-sensor 32 between the time that the reference detector 30 has signaled or otherwise identified at least the first reference point 50 (e.g. P1), and the occurrence of the corresponding outcome signal generated with respect to the associated production-device. For example, the outcome signal can be a switch signal from a programmable limit switch that is operatively associated with the cutting device 60.

In a particular configuration, the calibration factor can be determined by including an averaging of a first set of data points to compute a first reference value. In another configuration, the determining of the calibration factor can include an averaging of a second set of data points to compute a second reference value.

Additionally, the invention can further include a modifying of the calibration factor by employing a selected adjustment factor. The adjustment factor can be provided by a sampling of portions of the web 24 which have been provided with the production outcome. For example, the adjustment factor can be provided by sampling the individual articles produced from the web 24.

FIG. 3D shows a representative example of a shifted, reference-detector signal, where the signals from the reference detector 30 have been shifted by a selected amount with reference to the number line 90 that has been derived from the speed-sensor 32. It should be appreciated that theoretically, there is no upper limit on how far the reference signals can be shifted relative to the original number-line values of the signals generated by the reference detector 30. In particular arrangements, the reference detector signals can be shifted by a value which corresponds to a distance of approximately 10 meters or less. Such shifting can correspond to multiple article lengths.

The shifted, reference-data which can be derived from a combination of the data from the speed-sensor 32 and the reference data saved from the reference detector 30. In this manner, information generated by the selected, task-signaling device (e.g. the programmable limit switch 62) for a particular article or article length can be matched with corresponding information, which is related to the same article and has been previously generated by the reference detector 30 and saved by the computer 54. For each diaper or other article, there can be a particular number of phasing units, or shift value, which occurs between the time that information is generated by the reference detector 30 and the time that corresponding information is generated by the selected task-signaling device. In a particular aspect, the shift values from a selected number of data sets can be averaged by the computer 54 to help reduce the variability that may be introduced into the overall process and apparatus. This averaged shift value can employed to better match or otherwise correlate selected function-data (e.g. data from the PLS 62) with its corresponding set of reference data from the reference detector 30.

The selected function-data (e.g. the cutoff data from the programmable limit switch 62) can be employed in combination with the shifted reference data, as representatively shown in FIG. 3D. These signal data can, for example, be employed to compute the distance between the separation line 68 and its associated, consecutively occurring leading and trailing pad end edges.

The actual shift value that is operatively coordinated and combined with the data from the reference detector 30 can be established by a calibration procedure. In the calibration procedure, the computer can, for example, be employed to average information from a predetermined number of articles (e.g. approximately fifty articles) to compute a shift value which will produce a desired distance 86 between the cutoff or separation line 68 and the pad edge 64, and produce a desired distance 88 between the cutoff line 68 and the consecutively occurring pad edge 66 (e.g. FIG. 3A). This particular shift value can be held by the computer 54 until the method or apparatus of the invention is recalibrated. A detailed description of the computer calibration routine is set forth herein.

The output of the integral of the speed sensor signals over time are integers, and the integers can be illustrated as a number line 90, as representatively shown in FIG. 3C. When the signal from the reference detector 30 changes state (e.g. from "high" to "low"), indicating that the trailing edge of the pad passes the photo eye, the computer 54 can capture the position of the web in terms of the number line derived from the speed-sensor 32. This value is denoted by "P1" in FIG. 3C. Similarly, when the reference detector signal changes state from "low" to "high", indicating that the leading edge of the pad has passed the photo eye, the computer can again capture a second position of the web using the speed-sensor. This second value is denoted by "P2" in FIG. 3C. The difference between the two numbers, "P2−P1", is the length of the total end-seal when the web 24 is subjected to a tension, if any, exerted by the processing equipment.

At a transition edge when the PLS signal changes from high to low (or low to high, if desired), the computer can capture a position of the web 24 with respect to the number line 90 that has been derived from the speed-sensor 32. With reference to FIG. 3C, the relative position of the final cut (or other target point 22) can be denoted by "C". The value of "C" can operatively correspond to a relative position of the final cut determined with respect to the moving web 24.

It should be noted that if the reference detector 30 is located between zero and one article length from the final cutting device 60, then the value, "C−P1", represents the amount of web traveled (in length units) from the reference detector to the final cut. If the reference detector 30 is between one and two article-lengths from the final cut, then the value, "C−P1", determined from the immediately preceding cycle represents the amount of web traveled from the reference detector to the final cut. Similarly, if the reference detector is between two and three article lengths from the final cut, then the value, "C−P1", determined from two cycles earlier represents the amount of web traveled from the reference detector to the final cut. This concept can be easily extended to cover the cases when the reference detector 30 is between "n" and "n+1" article-lengths from the final cut. For the purposes of simplicity, the present discussion will use the scenario where the reference detector 30 is positioned between zero and one article-lengths from the cutting device 60.

To calculate the length of the front to back end-seal length (ESL), a calibration factor "K" can be employed. The ESL can correspond to the pad separation distance 80 (e.g. FIG. 3), and can be determined while the web 24 is subjected to any tension exerted by the processing equipment. Conceptually, the calibration factor K is shown in FIG. 3C. It is the distance a target spot on the web to be cut (but not yet cut) travels to the cutoff point. If the occurrence of the PLS signal does not precisely coincide with the actual cutting operation, the calibration factor K can be adjusted to compensate for any difference between the occurrence of the PLS signal and the occurrence of the actual cutting operation.

Although the calibration factor "K" can be calculated, an estimation method can be more effective due to the stochastic nature of the process. By employing the value of the calibration factor "K", the pad and end-seal signal can conceptually be shifted forward by the amount "K" to the final cut as shown in FIG. 3D. The leading and trailing end-seal lengths, also shown in FIG. 3D, can thus be calculated using the formulas:

Leading end-seal length=$(P2+K)-C$;

Trailing end-seal length=$C-(P1+K)=C-P1-K$.

To estimate the value of "K", it can be noted from FIG. 3C that "K" is the distance from the cutoff signal to the first edge of the pad signal plus the desired first (leading) end-seal length. Note that this first calculation does not use "P1". Similarly, "K" can also be calculated by the distance from the cut-off signal to the second edge of the pad signal minus the desired second (trailing) end-seal length. It is evident that this second calculation does not use "P2". To use information from both "P1" and "P2", the following values can be calculated:

$$E2 = C - P2; \text{ and}$$

$$ESL = P2 - P1.$$

Thus, the equation for "K" can be:

$$K = E2 + ESL - \text{target of the second (trailing) end-seal length}$$

Note: the target of the second end-seal length is the length that would be observed while the web is being subjected to the tension, if any, exerted by the processing equipment.

Since "E2" and ESL contain some random variations due to several factors such as raw materials, vibrations, sensor errors, imperfect equipment, etc., additional steps can be taken to improve accuracy. These steps can include:

1. Using a selected sample of the most recent consecutive data points (e.g. the most recent 64 data points), maintain averages and standard deviations of "E2" and ESL.
2. The 64 data points are considered normal if the calculated standard deviation is below a predetermined limit (e.g. 2 mm).
3. If the standard deviations of both E2 and ESL are low, then the estimated value of K is:

$$K = \text{average } E2 + \text{average } ESL - \text{target of trailing end-seal length}$$

Note: the target of the second end-seal length is the length that would be observed while the web is being subjected to the tension, if any, exerted by the processing equipment.

The measurements described thus far represent the end-seal lengths, as determined under any tension exerted on the web by the process. To ensure that the product articles meet specifications, the Quality Assurance personnel can regularly sample the articles and hand-measure the end-seal lengths. The average of the sum of the leading and trailing end-seal lengths is considered the actual end-seal length. To convert the computer measured data to the estimated cut end-seal lengths, a second calibration factor "D" can be employed. The second calibration factor can be the ratio of the computer measured, end-seal length and the actual end-seal length, as can be determined with the formula:

$$D = (\text{average } ESL)/(\text{average of hand-measured end-seal lengths}).$$

The final calculation formulas are:

$$K = \text{average } E2 + \text{average } ESL - (\text{target trailing end-seal length})/D$$

$$\text{Leading end-seal length} = (P2 + K - C) * D$$

$$\text{Trailing end-seal length} = (C - P1 - K) * D$$

The shown configuration of the invention can be employed to develop the end seal measurements representatively shown in FIG. 3. The first measurement can correspond to a first spacing distance 80 between the trailing edge 64 of a first pad and leading edge 66 of a next consecutive, second pad. The first spacing distance can correspond to an end-seal length (ESL) value. The second measurement can correspond to a trailing inset distance 86 between the first reference point 50 and the target point 22. For example, this measurement can correspond to a distance between the trailing edge 64 of a first pad and a desired separation line 68 (e.g. FIG. 2). The trailing inset distance may also be referred to as a "trailing end-seal length". The third measurement can correspond to a leading inset distance 88 between the target point 22 and a second reference point 52. For example, the third measurement can correspond to a trailing inset distance between the desired separation line 68 and the leading edge 66 of an immediately following pad. The leading inset distance may also be referred to as a "leading end-seal length".

A suitable comparator mechanism may be employed to compare various measured distances with selected, corresponding acceptance value ranges. For example, the comparator mechanism can comprise a part of the computer 54, and can be configured to compare the trailing end-seal length 86 to an acceptance value range. If the trailing end-seal 86 is too short, a reject signal can be generated to cull the particular, unacceptable article from the production lot. Similarly, any of the other measured lengths and distances can be compared to corresponding acceptance value ranges, and appropriate signals can be generated to direct mechanisms, such as a programmable controller 92 and a diverter 94, to cull individual, unacceptable articles from the production lot.

It should be noted that, in the representatively shown embodiment, the signal from the speed sensor 32 can be connected to a counter within computer 54, and the value of the counter can increase by one each time a falling edge of the signal occurs. This counting process can employ the signal from the speed sensor 32 to generate a distance measurement.

Referring to the reference detector signals illustrated in FIG. 3A and the number line illustrated in FIG. 3C, P1 represents the trailing end edge of a fluff pad, and P2 represents the leading end edge of the next consecutive pad. As discussed herein, a desired measurement objective can be to locate the edges P1 and P2 in terms of units of length. Once these values are obtained and appropriately combined with data from the speed sensor and the operating machinery positions, the method and apparatus of the invention can provide improved control of the operating machinery. The invention can more effectively detect and respond to dynamic changes in the web. Additionally, the invention can exhibit an improved ability to detect and cull defective products, thereby improving product quality.

To configure the method and apparatus of the invention to operatively employ the reference signal shown in FIG. 3A and the "final cut" or other product-device signal shown in FIG. 3B, a measurement system can be configured to capture the signal edges and the relative distance values that correspond to each of the signal edges. There are many techniques for accomplishing these operations, and any operative technique may be employed.

For example, the computer 54 may be configured to include a dedicated microprocessor, which can continuously scan the reference signal via conductor S34, and can continuously scan the final cut signal via conductor S52. When a change in signal state is detected, the microprocessor can read the counter (or integrator) and obtain the value which operatively represents the signal position. With reference to FIG. 3A, for example, the microprocessor can scan the reference signal from left to right starting when the reference signal is high. As soon as the reference signal changes states from high to low, indicating that edge 64 is detected, the microprocessor can read the value for P1 from the counter that represents the number line illustrated in FIG. 3C. When the reference signal changes state from low to high, indicating that edge 66 is detected, the microprocessor can read the value for P2 from the number line counter. Similarly, when the dedicated microprocessor detects that the final cut signal (FIG. 3B) has changed state from low to high (or high to low), the microprocessor can read the value C from the number line. As a result, the method and apparatus of the invention can provide an advantageous combination of accuracy, simplicity, and low cost.

In another configuration of the method and apparatus, the edges from the reference signal and the final cut signals can be captured by computer 54 by employing an interrupt technique. To do so, the input device where the reference signal and the final cut signal are connected can be programmed to generate an interrupt signal when a signal changes state. When computer 54 is interrupted, it can read the value of a counter (or integrator) and obtain the value that operatively represents the signal position. The reference signal representatively shown in FIG. 3A can be used to illustrate this task. As soon as the reference signal changes state from high to low, indicating that edge 64 is detected, the computer 54 is interrupted. The computer then reads the value P1 from the counter that represents the number line illustrated in FIG. 3C. When the reference signal changes state from low to high, indicating that edge 66 is detected, the computer 54 is again interrupted and the computer reads the value P2 from the number line counter.

Each of the described techniques can provide the value P1 representing edge 64, and the value P2 representing edge 66. Similarly, when the PLS signal shown in FIG. 3B, (or other production-device signal) changes state from low to high (or high to low), the production-device signal can generate an interrupt, and the computer can read the value of C on the number line shown in FIG. 3C. With conventional high-speed computers and microprocessors, the accuracy of the two methods can be similar, as long as the number of signals per product is not excessively large (e.g. less than 100). Accordingly, the selection of the method of measurement may be based on cost or other preference factors. For example, the interrupt system may be more readily incorporated into a manufacturing line that incorporates the configurations described in U.S. Pat. No. 4,837,715 entitled METHOD AND APPARATUS FOR DETECTING THE PLACEMENT OF COMPONENTS ON ABSORBENT ARTICLES by T. Ungpiyakul et al., which was issued Jun. 6, 1989.

Figure 5:
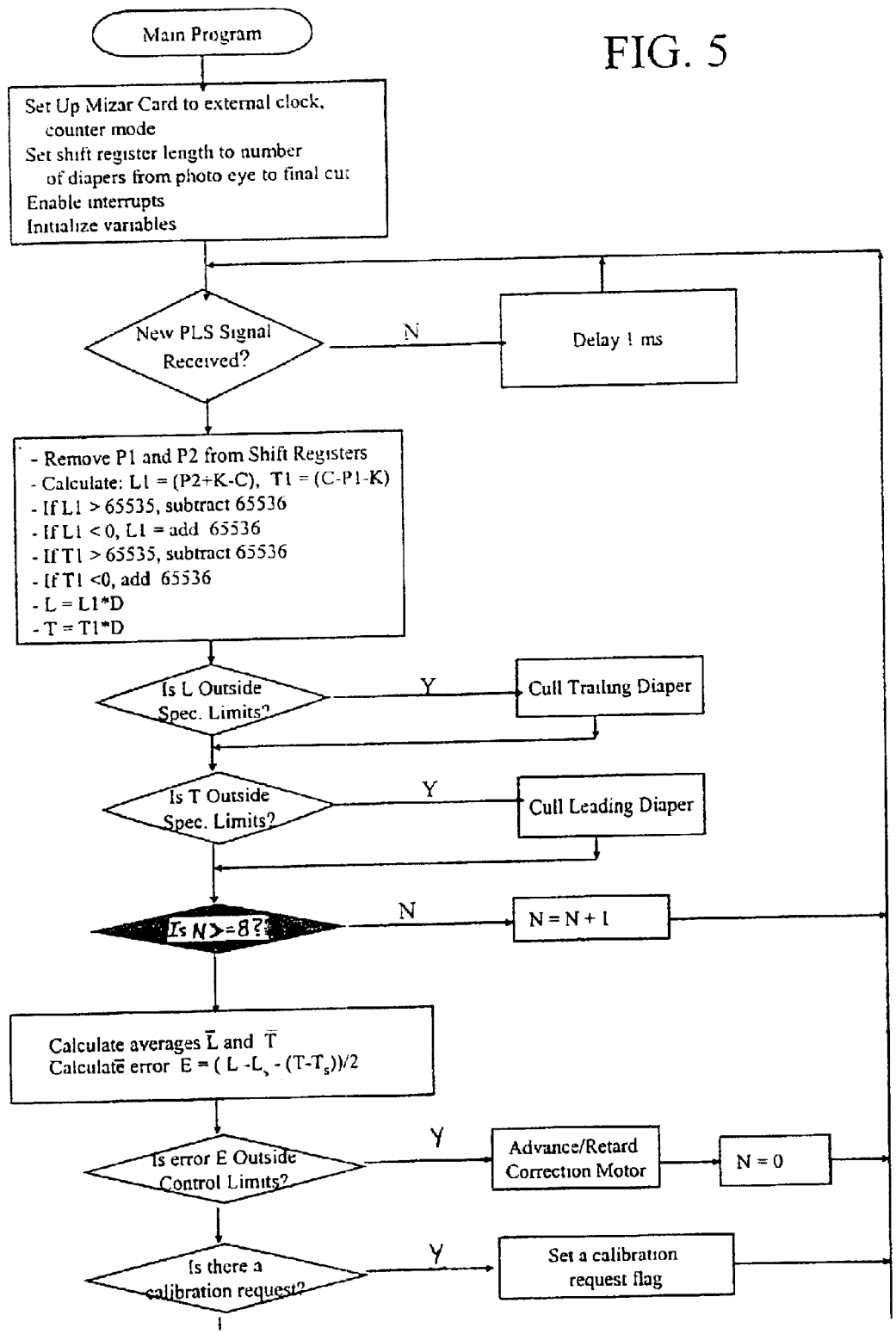
FIG. 5 shows a representative flow chart that outlines the operation of a measurement and control system that can be employed with the present invention.

The interrupt service routines can be illustrated and described with reference to the first portion of FIG. 5, FIG. 7, FIG. 7A, and FIG. 7B. A representative main program is illustrated in FIG. 5. The program can be setup to begin by configuring a timer/counter component (e.g. computer card) to use an external clock in a counter mode. In this case, the signals in the form of pulse train from the speed-sensor can serve as the external clock. Since this device is set in the counter mode, each time a pulse edge is received, the counter value increases by one. The counter, therefore, can perform an integration of the speed-sensor signal to generate a length signal. The length signal is conceptually illustrated as the number line 90 in FIG. 3C. The program can now receive interrupts from the edges of the reference signal (e.g. FIGS. 7 and 7A), and the selected production-device signal, such as provided by the final cut, PLS signal (e.g. FIG. 7B). These three interrupt tasks can, for example, be employed to provide the measurements needed to calculate the end seal lengths. With current, conventional technology, the interrupts can be very reliable, and the interrupt service routines can be less complex than prior routines, such as those described in U.S. Pat. No. 4,837,715.

As illustrated in FIG. 7, for example, when the signal changes from high to low, a falling edge interrupt is generated and the interrupt service routine changes the interrupt sense from falling edge to rising edge, reads the value P1, places the P1 value on a shift register, clears the interrupt and ends the routine. The shift register is a FIFO (first in first out) buffer that is used to transport edge data from the speed-sensor 32 for use in operating a desired production-device, such as the device which generates a final cut. If, for example, the distance between the speed-sensor 32 and the final cut is between 0–1 product-interval, then the shift register is not required. If the distance between the speed-sensor 32 and the final cut is between 1–2 product-intervals, then the shift register length is 1. If the distance between speed-sensor 32 and the final cut is between 2–3 product-intervals, then the shift register length is 2. If the distance between the speed-sensor 32 and the final cut is between n to n+1 product-intervals, then the shift register length is n.

FIG. 7A illustrates the rising edge interrupt, when the signal changes from low to high, a rising edge interrupt is generated, and the interrupt service routine changes the interrupt sense from rising edge to falling edge, reads the value P2, places the P2 value in the shift register, clears the interrupt and ends the routine.

With reference to FIG. 7B, a selected production-device (e.g. final cut mechanism) can provide a corresponding production-device or production-outcome signal (e.g. PLS signal). In the representatively shown arrangement, a designated edge (rising or falling) of the PLS (final cut) signal generates an interrupt. The interrupt service routine reads the value C, stores the C value, sets a flag to indicate that the new PLS signal has been received, clears the interrupt and ends the routine.

With reference to FIG. 5, the main program can be configured to detect that a new or updated production-device signal (e.g. final-cut PLS signal) has been received. The program can then process the fresh data by taking the corresponding P1 and P2 values from output of the shift register, and calculating the value of the leading and trailing end-seal lengths, as described herein:

Leading end-seal length=$(P2+K-C)*D$

Trailing end-seal length=$(C-P1-K)*D$

Prior to a first calibration, the value of D is initialized to 1, and the value for K is initialized using the first measured values of P1, P2, and C. In addition, the program is configured to adjust for the "rollover" phenomenon that occurs when the counter is at one count over its maximum. For illustration, assume that a 3 bit counter is used; then the counter is initialized at 0 and it will count correctly for the first 7 pulses it receives. When the 8th pulse is received, the counter will read 0 because of the "rollover" phenomenon. If we want the distance between the 7th and the 2nd pulse, we would calculate it as 7−2=5, which is correct. However, if we want the distance between the 8th and the 2nd pulse, the value of 0−2 is not correct. Because of the rollover, the counter reading of 0 actually represents 8 (10 in octal representation). The correct value, therefore, is 8+0−2=6. In summary, the calculation resulting in a value less than 0 or greater than the maximum counter value indicating that a "rollover" has occurred and correction is required. In the representatively shown arrangement, the 16 bit counter can be used for simplicity while providing adequate performance. If the 16 bit counter is not sufficient, a 24 or 32 bit counter can be used with minor adjustment. In the case of 16 bit counter, the algorithm for handling the "rollover" phenomenon can be as follows:

1. Calculate:

a. $L1=P2+K-C$ b. $T1=C-P1-K$

2. If L1 is greater than 65535, then the data is greater than the maximum counter value and 65536 is subtracted from it. Similarly, if L1 is less than 0, then 65536 is added to it. This procedure is repeated until the values are within the range of 0 to 65535.
3. If T1 is greater than 65535, then the data is greater than the maximum counter value and 65536 is subtracted from it. Similarly, if T1 is less than 0, then 65536 is added to it. This procedure is repeated until the values are within the range of 0 to 65535.
4. The leading and trailing end-seal lengths are then calculated using the formula:

$$L = \text{Leading end-seal length} = (P2 + K - C) * D = L1 * D$$

$$T = \text{Trailing end-seal length} = (C - P1 - K) * D = T1 * D$$

The program can then check whether or not the value of the leading end-seal length is outside the specification limit. If it is outside the limit, the product can be culled. Similarly, the program checks whether the value of trailing end-seal length is outside the specification limit, and can cull the product if it is out of specification.

The registration control in a personal care product manufacturing process (e.g. a diaper manufacturing process) may be a regulator, instead of a servo controller. A regulator controller expects the reference signal (target) to be relatively constant while a servo controller expects the reference signal to change quickly and often. For regulatory control, many control schemes such as PID (Proportional Integral Derivative), Minimum Mean Squared Error, and Optimal Control can be used. Such techniques are conventional, and well known to those skilled in control-theory. From experience, it has been determined that a proportional control using a running average of errors (which is the same as running average of data minus target) can be sufficient. This control scheme is desired because it is effective and readily understood by people who have limited experience in control theory. On the basis of this information, the program can calculate the average values of the leading and trailing end-seal lengths. In most cases, a sample size between 4 and 16 can be sufficient for regulatory control purpose. The sample size chosen for the representatively shown arrangement is 8, and with reference to the flow chart shown in FIG. 5, the method and apparatus can calculate the averages of the leading and trailing end-seal lengths for the latest 8 products. After the averages are calculated, the program can check whether or not the end-seal lengths are sufficiently close to their target values, based on a predetermined tolerance limit. If they are not, the control action signal can be issued to a correction motor to advance or retard the final cut operation (or other production-device operation) as appropriate. If a control action is taken, the software can then wait for a subsequent 8 products before the next calculation is conducted, to ensure that the averages contain data that has been obtained after the correction was made.

Figure 6:
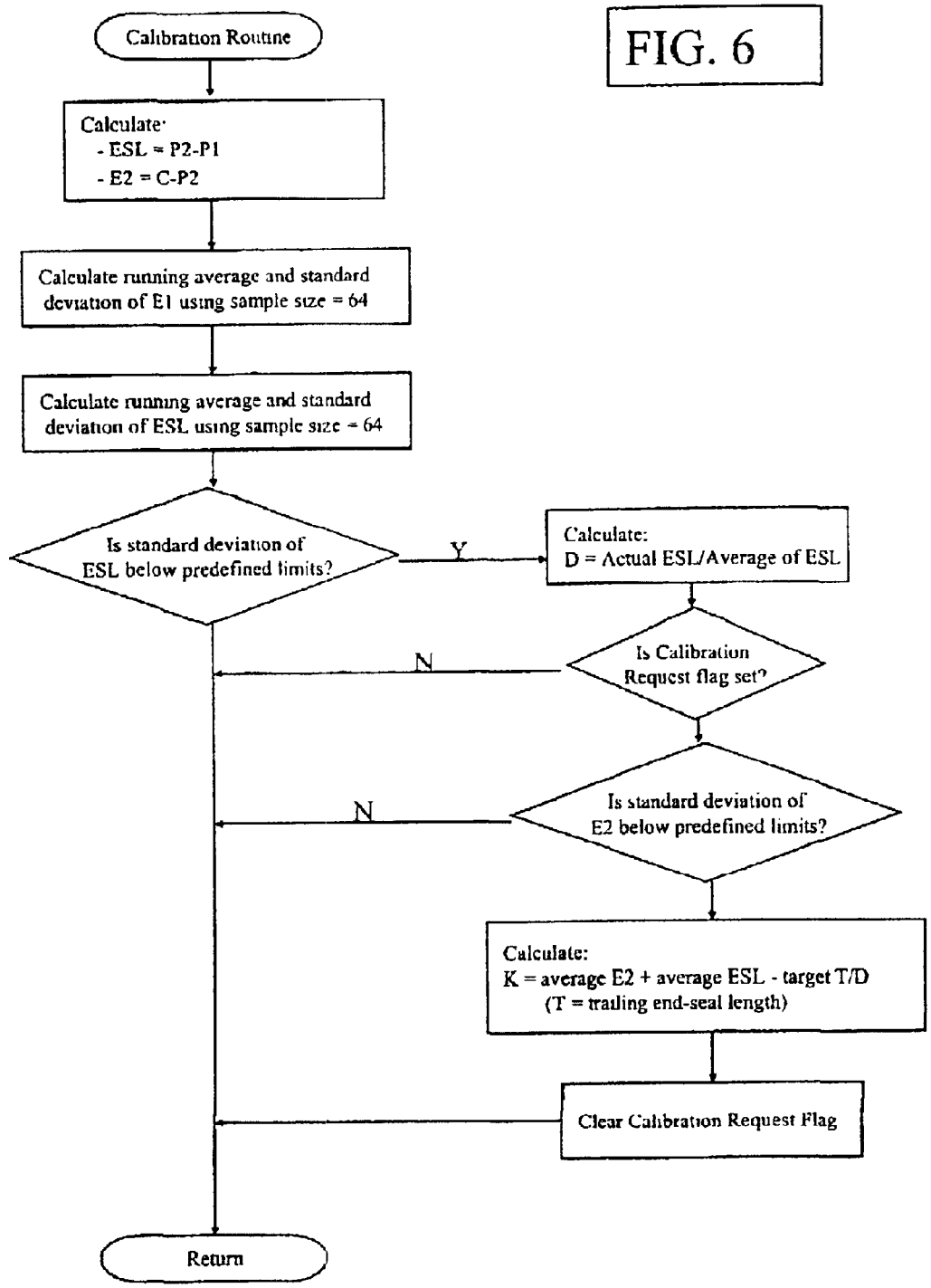
FIG. 6 shows a representative flow chart that outlines the operation of a calibration system that can be employed with the present invention.

After the program finishes the control algorithm execution, the program can check whether or not a calibration action is requested. If so, the program can activate a calibration algorithm by setting a flag to indicate that a recalibration has been requested. A representative calibration algorithm is shown in FIG. 6. The program can calculate the total end-seal length (ESL) and the back end-seal length, E2, using the formula:

$$ESL=P2-P1$$

$$E2=C-P2$$

Using the latest 64 articles or products, for example, the program can calculate the running averages and standard deviations of the back end-seal length E2 and the total end-length ESL. The sample size of 64 has been found to be adequate for a process that converts personal care articles such as diapers. Other operative values may be selected for other converting processes. The standard deviations are calculated so that they can be used to detect abnormalities in the data. If there is no abnormality in the data, then the standard deviations would be smaller than their predetermined limits. If at least the one of the two standard deviations is higher than its limit, the program can wait for the arrival of the next set of data where the older set of sample data are replaced by the newest set of sample data. If the standard deviation limits are appropriately set, then the two standard deviation values will be lower than the limits that were set to determine a condition where the process is substantially free of excessive disturbances. If the standard deviation of ESL is lower than its limit, the program can be configured to calculate a second calibration factor D, as follows:

$$D=(\text{average } ESL)/(\text{average of hand-measured end-seal lengths}).$$

The program can then check whether or not a calibration has been requested by checking whether or not the calibration flag is set. If set, then the program can check to ensure that the standard deviation of E2 is below its limit before the program calculates the calibration factor "K" using the equation:

$$K=\text{average } E2+\text{average } ESL-\text{target of trailing end-seal length}$$

The program can then clear the calibration request flag to indicate that the calibration process is complete.

An article tracking scheme can be employed to generate a shifted position signal (e.g. FIG. 3D). In the shown configuration of the invention, this tracking scheme can employ two assumptions. The first assumption is that the separation between the reference detector 30 and the selected production-operation or production-device can be determined. The second assumption is that the phase between the reference detector 30 and the task-signal or function-data (e.g. the cutoff signal from the programmable limit switch 62) will not change by more than one-half of the length of an article. On the basis of these assumptions, edge P1 can be tracked as follows: The edges measured at P1 can be placed in a first-in-first-out (FIFO) buffer that can be used to transport edges from sensor 32 to their corresponding final cut signal (or other selected production-device signal). If the distance between the speed-sensor 32 and the operation of the final cut mechanism is between 0–1 product, then the FIFO buffer is not required and the data can be used immediately. If the distance between the sensor 32 and the final cut is between 1–2 products, then the length of the FIFO buffer is 1. If the distance between the sensor 32 and the final cut operation is between 2–3 products, then the length of the FIFO buffer is 2. If the distance between the speed-sensor 32 and the final cut operation is between 3–4 products, then the length of the FIFO buffer is 3. If the distance between the sensor 32 and the final cut operation is between n and n+1 products, then the length of the FIFO buffer is n. The measurement program that generates the measurement of the P1 value can provide its data once per article. Similarly, the signal-generating device that provides data for the value C can also provide its data once per article. In the arrangement where the FIFO buffer length is 1, when a new P1 value is placed on the buffer, the previous value can be pushed out to an output buffer. When the measurement of C takes place, the program can read the value of P1' from the output buffer. Since the distance between sensor 32 and the final cut operation is between 1–2 products, it is clear that the value of P1' in this case can represent the edge of pad corresponding to the end-seal that is about to be cut. In the arrangement where the FIFO buffer length is 2, when a new P1 is placed on the buffer, the value of the measurement that happened two articles ago is pushed out to the output buffer. When the measurement of C takes place, it reads the value of P1" from the output buffer. Since the distance between the speed-sensor 32 and the final cut operation is between 2–3 products, it is clear that, in this case, the value of P1" represents the edge of pad corresponding to the end-seal that is about to be cut. This is a tracking scheme that can be extended to cover any distance between sensor 32 and the final cut operation, or to cover any signal-generating device.

Various cull outputs can be generated by the inspection aspect of a cull routine. For example, a first output can be generated when trailing end-seal length 86 is less than a specified minimum limit. A second output can be generated when leading end-seal length 88-is less than a specified minimum limit. Such a condition can occur when either one of the end-seal distances is too short.

In one configuration of the invention, the cull output can be normally "off", and the cull subroutine can turn the cull output "on" when a defective article is detected. Alternatively, as employed in the illustrated configuration, the cull output can be arranged to be normally "on", and can then be turned "off" when an acceptable article is detected. This second method technique can provide several advantages. In particular, articles will be culled if the hardware fails, signals are missing, or if the computer software cannot keep up with the apparatus machine speed.

Some personal care products have one or more waist members 102, and the waist members may or may not be elastomeric. In particular arrangements, the waist members can be initially applied as a single piece in the end-seal region of a corresponding product web 24. FIG. 8 representatively shows the top view of a diaper web having an initial, single-piece waist member, and FIG. 8A shows a representative side view of the web illustrated in FIG. 8. FIGS. 9 and 9A also show the line along which the web 24 is appointed to be cut into individual articles (e.g. diapers). It is evident that the initial, single elastic member will be cut into two pieces with one piece in the "back", trailing section of a first article and the other piece in the "front", leading section of another, second article. The waist members on the web 24 can be readily detected by employing known, conventional techniques. For example, suitable technology has been disclosed in U.S. Pat. No. 4,837,715 entitled METHOD AND APPARATUS FOR DETECTING THE PLACEMENT OF COMPONENTS ON ABSORBENT ARTICLES by T. Ungpiyakul et al., which was issued Jun. 6, 1989.

FIG. 9 shows the side view of the web 24 having at least one, a desirably a series, of the initial, single-piece waist members 102. FIG. 9 is similar to FIG. 3. In addition, FIG. 9A, FIG. 9B, FIG. 9C, and FIG. 9D are similar to FIG. 3A, FIG. 3B, FIG. 3C, and FIG. 3D. In particular:

1. The waist member reference signal shown in FIG. 9B is similar to the Reference Signal shown in FIG. 3B.
2. The final cut PLS signal shown in FIG. 9B is the same as that shown in FIG. 3B.
3. The number line (in millimeters) shown in FIG. 9C the same as that shown in FIG. 3C.
4. The shifted waist member signal shown in FIG. 9D is similar to the shifted Reference Signal shown in FIG. 3D.
5. The values K*, P1*, P2*, and C* shown in FIGS. 9C and 9D are similar to K, P1, P2, and C in FIGS. 3C and 3D.

It is, therefore, readily apparent that the disclosed method and apparatus that are employed to calculate the length of the leading and trailing end-seal lengths can alternatively be employed to calculate the "width" (length along the movement direction 26) of the front and back waist member sections. After the widths of waist member sections are calculated, the computer can be programmed to cull the articles (e.g. diapers) if the widths of their waist member sections are outside the predetermined specification limits.

As representatively shown in FIGS. 10 and 10A, the method and apparatus of the invention can be configured to provide a final cut or other production-operation when the web 24 includes two individual, waist member pieces 102a that are arranged and attached between two successive pads 70. It is readily apparent that the technique and system of the invention that have been employed to calculate the lengths of the end-seals, and/or the widths of the waist member sections can be used to calculate any relative position between any two components. For example, the technique and system of the invention can be employed to calculate the distances between the waist members and the edges of associated absorbent pads. They can also be used to calculate the distance between the leg elastic members and the edges of their associated absorbent pads. They can further be used to calculate the distance between the fastening devices (e.g. adhesive tapes or mechanical fasteners) and the edges of absorbent pads. They can additionally be used to calculate the distance between a fastening device component (e.g. the landing zone, loop material of a hook-and-loop fastening system) and the edges of corresponding absorbent pads. The technique and system can further be used to calculate the distance between first and second components of a fastening system. Optionally, the technique and system of the invention can be employed to calculate a distance between a leg elastic members and a waist elastic member.

Having thus described the invention in rather full detail, it will be readily apparent that various changes and modifications can be made without departing from the spirit of the invention. All of such changes and modifications are contemplated as being within the scope of the invention, as defined by the subjoined claims.

What is claimed is:

1. A method for controlling a registration between a target point on a moving web, and a production outcome provided by a production operation, said method comprising:

a transporting of said web along a movement direction past a reference detector;

a detecting of at least a first reference point on said web;

a designating of said target point on said web by employing at least said first reference point on said web;

a transporting of said web past a speed-sensor;

a substantially continuous measuring of a web speed of said moving web at said speed-sensor to provide web speed data;

an integrating of said web speed data over time to determine a web-length which has been transported past said speed-sensor;

an actuating of said production outcome; and an adjusting of said actuating of said production outcome.

2. A method as recited in claim 1, wherein said measuring of said web speed includes a substantially non-contact measuring of said web speed.

3. A method as recited in claim 2, wherein said measuring of said web speed employs a Doppler-related measurement.

4. A method as recited in claim 2, wherein said measuring of said web speed employs a Doppler-related measurement produced with a laser.

5. A method as recited in claim 1, wherein said adjusting of said actuating of said production outcome is provided after a reference-length of said web has been transported past said speed-sensor.

6. A method as recited in claim 1, further including a detecting of at least a second reference point on said web.

7. A method as recited in claim 1, further including a providing of at least one outcome datum which operatively represents said actuating of said production outcome.

8. A method as recited in claim 1, further including actuating said production outcome at a production-device; and spacing said speed-sensor away from a production-device by a selected offset distance along said movement direction.

9. A method as recited in claim 8, further including a spacing of said speed-sensor away from said production-device by a selected offset distance which is not more than about 1 meter.

10. A method as recited in claim 1, further including a stabilizing of said web at a web-control mechanism.

11. A method as recited in claim 1, further including a positioning of said web-control mechanism at a location which is proximate said speed-sensor.

12. A method as recited in claim 1, wherein said actuating of said production outcome includes a cutting of said moving web.

13. A method as recited in claim 1, wherein said actuating of said production outcome includes an applying of a separately provided component onto said moving web.

14. A method as recited in claim 1, wherein said actuating of said production outcome includes a changing of a speed of said web at a production-device.

15. A method as recited in claim 1, wherein said actuating of said production outcome includes a changing of an operating speed of a production-device.

16. A method as recited in claim 1, wherein said adjusting of said actuating of said production outcome includes a regulating of said reference-length by employing a calibration factor.

17. A method as recited in claim 1, further including a determining of a calibration factor by including an averaging of a first set of data points to compute a first reference value.

18. A method as recited in claim 17, wherein said determining of said calibration factor includes an averaging of a first set of data points to compute a first reference value, and an averaging of a second set of data points to compute a second reference value.

19. A method as recited in claim 18, wherein said method further includes a modifying of said calibration factor by employing an adjustment factor which has been provided by a sampling of portions of said web which have been provided with said production outcome.

20. An apparatus for controlling a registration between a target point on a moving web, and a production outcome provided by a production operation, said apparatus comprising:

a transporter which can move said web along a movement direction past a reference detector, said reference detector configured to detect at least a first reference point on said web, said first reference point configured for employment to designate said target point on said moving web;

a speed-sensor, past which said web can be transported, said speed-sensor capable of substantially continuously measuring a web speed of said moving web to provide web speed data;

an integrator which can operate on said web speed data over time to determine a web-length which has been transported past said speed-sensor;

a production-device which can be actuated to provide said production outcome; and a regulating system which can adjust an actuating of said production outcome.

* * * * *